US012638443B2

(12) United States Patent
Huang et al.

(10) Patent No.: US 12,638,443 B2
(45) Date of Patent: May 26, 2026

(54) CARTRIDGE AND ANALYZER FOR FLUID ANALYSIS

(71) Applicant: Taiwan Semiconductor Manufacturing Co., Ltd.

(72) Inventors: Jui-Cheng Huang, Hsinchu (TW); Chin-Hua Wen, Miaoli (TW); Tung-Tsun Chen, Hsinchu (TW); Cheng-Hsiang Hsieh, Taipei (TW); Yu-Jie Huang, Kaohsiung (TW); Ching-Hui Lin, Hsinchu (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 1279 days.

(21) Appl. No.: 17/314,825

(22) Filed: May 7, 2021

(65) Prior Publication Data

US 2021/0263022 A1     Aug. 26, 2021

Related U.S. Application Data

(62) Division of application No. 15/406,066, filed on Jan. 13, 2017, now Pat. No. 11,119,101.

(Continued)

(51) Int. Cl.
*G01N 33/543* (2006.01)
*B01L 3/00* (2006.01)
(Continued)

(52) U.S. Cl.
CPC .... *G01N 33/5438* (2013.01); *B01L 3/502715* (2013.01); *C12Q 1/6837* (2013.01);
(Continued)

(58) Field of Classification Search
CPC ............. G01N 33/5438; G01N 27/414; G01N 27/416; B01L 3/502715; B01L 2200/027;
(Continued)

(56) References Cited

U.S. PATENT DOCUMENTS 5,232,109 A     8/1993 Tirrell et al.
8,337,683 B2     12/2012 Choi et al.
(Continued)

FOREIGN PATENT DOCUMENTS

CN     1981186 A     6/2007
CN     101592627 A     12/2009
(Continued)

OTHER PUBLICATIONS

Lin, Yen-Heng, and Po-Yu Peng. "Semiconductor sensor embedded microfluidic chip for protein biomarker detection using a bead-based immunoassay combined with deoxyribonucleic acid strand labeling." Analytica Chimica Acta 869 (2015): 34-42. (Year: 2015).*
(Continued)

*Primary Examiner* — Robert J Eom
(74) *Attorney, Agent, or Firm* — Sterne, Kessler, Goldstein & Fox P.L.L.C.

(57)     ABSTRACT

A fluidic cartridge and methods of operation are described. The fluidic cartridge includes a substrate having a plurality of contact pads designed to electrically couple with an analyzer, a semiconductor chip having a sensor array, and a reference electrode. The fluidic cartridge includes a first fluidic channel having an inlet and coupled to a second fluidic channel, the second fluidic channel being aligned such that the sensor array and the reference electrode are disposed within the second fluidic channel. A first plug is disposed at the first inlet. The first plug includes a compliant material configured to be punctured by a capillary without leaking fluid through the first plug.

20 Claims, 17 Drawing Sheets

Related U.S. Application Data

(60) Provisional application No. 62/372,596, filed on Aug. 9, 2016.

(51) Int. Cl.
| | |
|---|---|
| *C12Q 1/6837* | (2018.01) |
| *G01N 27/414* | (2006.01) |
| *G01N 27/416* | (2006.01) |

(52) U.S. Cl.
CPC ......... *G01N 27/414* (2013.01); *G01N 27/416* (2013.01); *B01L 2200/027* (2013.01); *B01L 2300/044* (2013.01); *B01L 2300/0636* (2013.01); *B01L 2300/0645* (2013.01); *B01L 2300/0819* (2013.01); *B01L 2300/0867* (2013.01); *B01L 2300/087* (2013.01); *B01L 2400/0683* (2013.01)

(58) Field of Classification Search
CPC ....... B01L 2300/044; B01L 2300/0636; B01L 2300/0645; B01L 2300/0819; B01L 2300/0867; B01L 2300/087; B01L 2400/0683; C12Q 1/6837
See application file for complete search history.

(56) References Cited

U.S. PATENT DOCUMENTS

| | | | |
|---|---|---|---|
| 8,518,662 | B2 | 8/2013 | Ritzen et al. |
| 8,574,919 | B2 | 11/2013 | Ramel et al. |
| 8,900,440 | B2 | 12/2014 | Nebling et al. |
| 9,091,647 | B2 | 7/2015 | Chang et al. |
| 9,823,218 | B2 | 11/2017 | Klootwijk et al. |
| 2010/0289483 | A1 | 11/2010 | Immink et al. |
| 2013/0200438 | A1 | 8/2013 | Liu et al. |
| 2014/0252421 | A1 | 9/2014 | Liu et al. |
| 2015/0060303 | A1 | 3/2015 | Blohm et al. |
| 2016/0016171 | A1 | 1/2016 | Goel |
| 2016/0091509 | A1 | 3/2016 | Di Tullio et al. |
| 2017/0059589 | A1 | 3/2017 | Okamoto et al. |

FOREIGN PATENT DOCUMENTS

| | | | |
|---|---|---|---|
| CN | 101896829 | A | 11/2010 |
| CN | 102215965 | A | 10/2011 |
| CN | 103675024 | A | 3/2014 |
| CN | 104781658 | A | 7/2015 |
| CN | 105142789 | A | 12/2015 |
| DE | 693 04 797 | T2 | 4/1997 |
| DE | 10 2008 027 038 | A1 | 12/2009 |
| DE | 10 2012 205 171 | B3 | 9/2013 |
| JP | 2006-308428 | | 11/2006 |
| KR | 2009-0011557 | | 2/2009 |
| TW | 201541080 | A | 11/2015 |
| WO | WO 2014/096977 | A2 | 6/2014 |
| WO | WO 2016/049533 | A1 | 3/2016 |
| WO | WO 2016/100521 | A1 | 6/2016 |

OTHER PUBLICATIONS

Barik, Mohammad Abdul, Rashmi Deka, and Jiten Chandra Dutta. "Carbon nanotube-based dual-gated junctionless field-effect transistor for acetylcholine detection." IEEE Sensors Journal 16.2 (2015): 280-286. (Year: 2015).*

Agoulmine, Nazim, et al. "Enabling communication and cooperation in bio-nanosensor networks: toward innovative healthcare solutions." IEEE Wireless Communications 19.5 (2012): 42-51. (Year: 2012).*

Lin, Yen-Heng, et al. "Integrating solid-state sensor and microfluidic devices for glucose, urea and creatinine detection based on enzyme-carrying alginate microbeads." Biosensors and Bioelectronics 43 (2013): 328-335. (Year: 2013).*

Ly, Jimmy, et al. "Automated reagent-dispensing system for microfluidic cell biology assays." Journal of Laboratory Automation 18.6 (2013): 530-541. (Year: 2013).*

Buitrago, Elizabeth, et al. "The top-down fabrication of a 3D-integrated, fully CMOS-compatible FET biosensor based on vertically stacked SiNWs and FinFETs." Sensors and Actuators B: Chemical 193 (2014): 400-412.

Spijkman, Mark-Jan, et al. "Dual-gate organic field-effect transistors as potentiometric sensors in aqueous solution." Advanced Functional Materials 20.6 (2010): 898-905.

Saarela, Ville, et al. "Re-usable multi-inlet PDMS fluidic connector." Sensors and Actuators B: Chemical 114.1 (2006): 552-557.

Kang, Edward, et al. "A hemispherical microfluidic channel for the trapping and passive dissipation of microbubbles." Journal of Micromechanics and Microengineering 20.4 (2010): 045009.

Evander, Mikael, and Maria Tenje. "Microfluidic PMMA interfaces for rectangular glass capillaries." Journal of Micromechanics and Microengineering 24.2 (2014): 027003. (Year: 2014).

Liu, Robin H., et al. "Fully Integrated Microfluidic Biochips for DNA Analysis." International Journal of Computational Engineering Science 4.02 (2003): 145-150. (year: 2003).

Verpoorte, Elisabeth MJ, et al. "Three-dimensional micro flow manifolds for miniaturized chemical analysis systems." Journal of Micromechanics and Microengineering 4.4 (1994): 246.

Huang, I-Yu, and Ruey-Shing Huang. "Fabrication and characterization of a new planar solid-state reference electrode for ISFET sensors." Thin solid films 406. 1-2 (2002): 255-261.

German Office Action directed toward related application No. DE 10 2017 103 469.2, mailed from the German Patent Office, dated Sep. 15, 2017; 10 pages.

Ellington, A.D., et al.: In vitro selection of RNA molecules that bind specific ligands. In: Nature. 1990, Bd. 346, H. 6287, S. 818- 822. ISSN 0028-0836 (p); 1476-4687 (e). DOI: 10.1038/346818a0. URL: http://www.nature.com/nature/journal/v346/n6287/pdf/ 346818a0. pdf [accessed Jan. 31, 2014]. http://www.nature .com/ nature/journal/v346/n6287/abs/346818a0. html [accessed Jan. 31, 2014]; 5 pages.

Goldsby, Richard A., et al.: Immunology. 4. ed. New York: Freeman, 2000. S. 83-113.—ISBN 0-7167-3331-5; 33 pages.

Lo, R., et al.: Reusable, adhesiveless and arrayed in-plane microfluidic interconnects. Journal of Micromechanics and Microengineering, 2011, 21. Jg., Nr. 5, S. 054021; 14 pages.

Moschou, Despina [u.a.] et al.: Surface and Electrical Characterization of Ag/AgCI Pseudo-Reference Electrodes Manufactured with Commercially Available PCB Technologies. In: Sensors. vol. 15, 2015, H. 8, S. 18102-18113.—ISSN 1424-8220. doi:10.3390/ s150818102; 12 pages.

Ng, E. WM, et al.: Pegaptanib, a targeted anti-VEGF aptamer for ocular vascular disease. Nature Reviews Drug Discovery, 2006, 5. Jg., Nr. 2, S. 123-132. https://www.researchgate.net/profile/Perry_ Calias2/publication/7260480_Pegaptanib_a_targeted_anti-VEG F:... aptamer _for_ ocular_ vascular_disease/links/0c960521362ff78e8d 000000.pdf; 10 pages.

Temiz, Y., et al.: Lab-on-a-chip devices: How to close and plug the lab? Microelectronic Engineering, 2015, 132. Jg., S. 156-175. https://doi.org/1_0.1016/j.mee.2014.1_0.013; 20 pages.

Tuerk, C. et al.: Systematic evolution of ligands by exponential enrichment: RNA ligands to bacteriophage T4 DNA polymerase. In: Science. 1990, Bd. 249, H. 4968, S. 505-510. ISSN 0036:-8075 (p); 1095-9203 (e). DOI: 10.1126/science.2200121. URL: http://www. sciencemag.org/contenV249/4968/505.full.pdf?sid=aed 113f7 -fdaf-45de-89be-617946014c72 [accessed Jan. 31, 2014]; 6 pages.

Wagler, P.F. et al.: General-Purpose, parallel and reversible microfluidic interconnects. IEEE Transactions on Components, Packaging and Manufacturing Technology, 2015, 5. Jg., Nr. 3, S. 291-300; 10 pages.

Office Action, dated Nov. 16, 2020, for German Intellectual Property Office Appl. No. 10 2017 103 469.2, 12 pages.

\* cited by examiner

1300

FLOW FIRST SOLUTION THROUGH FIRST CHANNEL — 1302

CALIBRATE SENSOR IN FIRST SOLUTION — 1304

INPUT SAMPLE VIA SAMPLE INLET — 1306

FLOW SECOND SOLUTION THROUGH SECOND CHANNEL — 1308

INCUBATE BIOMOLECULES OVER SENSOR REGION — 1310

FLOW THIRD SOLUTION TO TRANSPORT SAMPLE INTO WASTE CHAMBER — 1312

MEASURE SENSOR OUTPUT — 1314

CARTRIDGE AND ANALYZER FOR FLUID ANALYSIS

CROSS-REFERENCE TO RELATED APPLICATIONS

This application is a divisional of U.S. patent application Ser. No. 15/406,066, filed on Jan. 13, 2017, which claims priority of U.S. Provisional Patent Application No. 62/372,596, filed Aug. 9, 2016, each of which is incorporated by reference in its entirety.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

The interaction of the biological sample itself and the biosensor can be a challenge. Typically, a fluid containing the biological sample is pipetted directly over the sensing portion of the biosensor. This method leads to a large portion of the fluid sample not being used, and is time consuming to manually load each sensing area.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
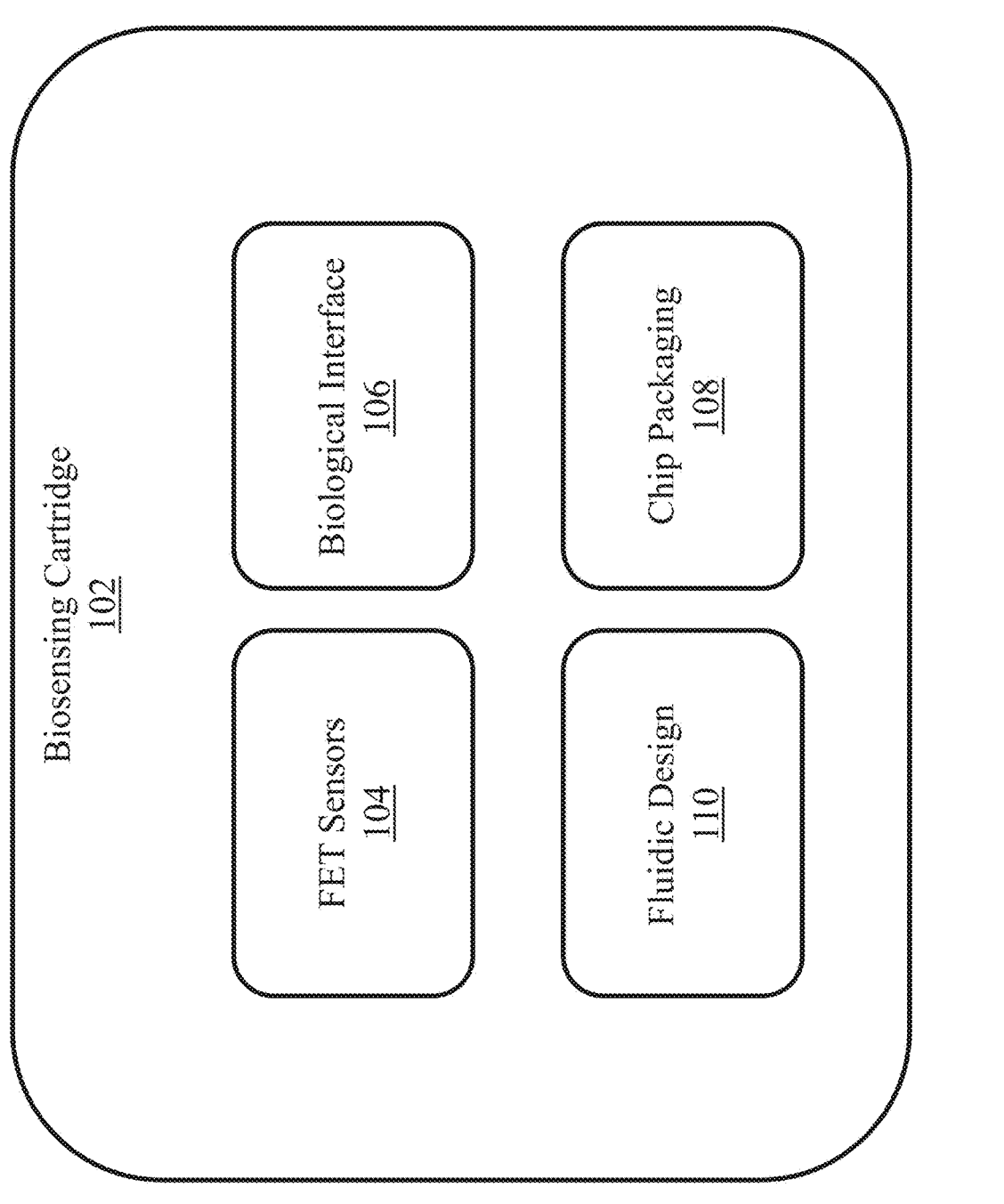
FIG. 1 is a diagram illustrating components of an exemplary biosensing cartridge.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed and/or disposed between the first and second features, such that the first and second features may not be in direct contact. In addition, the present disclosure may repeat reference numerals and/or letters in the various examples. This does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Terminology

Unless defined otherwise, all technical and scientific terms used herein have the same meanings as commonly understood by one of ordinary skill in the art to which this disclosure belongs. Although any methods and materials similar or equivalent to those described herein can be used in the practice or testing of embodiments in accordance with the disclosure; the methods, devices, and materials are now described. All patents and publications mentioned herein are incorporated herein by reference for the purpose of describing and disclosing the materials and methodologies which are reported in the publications which might be used in connection with the invention.

The acronym "FET," as used herein, refers to a field effect transistor. A very common type of FET is referred to as a metal oxide semiconductor field effect transistor (MOSFET). Historically, MOSFETs have been planar structures built in and on the planar surface of a substrate such as a semiconductor wafer. But recent advances in semiconductor manufacturing have resulted in three-dimensional, of fin-based, MOSFET structures.

The term "bioFET" refers to a FET that includes a layer of immobilized capture reagents that act as surface receptors to detect the presence of a target analyte of biological origin. A bioFET is a field-effect sensor with a semiconductor transducer, according to an embodiment. One advantage of bioFETs is the prospect of label-free operation. Specifically, bioFETs enable the avoidance of costly and time-consuming labeling operations such as the labeling of an analyte with, for instance, fluorescent or radioactive probes. One specific type of bioFET described herein is a dual-gate back-side sensing bioFET. The analytes for detection by a BioFET will normally be of biological origin, such as—without limitation—proteins, carbohydrates, lipids, tissue fragments or portions thereof. However, in a more general sense a BioFET is part of a broader genus of FET sensors that may also detect any chemical compound (known in the art as a ChemFET), or any other element, including ions, such as protons or metallic ions (known in the art as an ISFET). This invention is meant to apply to all types of FET-based sensors ("FET Sensor"). One specific type of FET Sensor herein is a Dual-Gate Back Side Sensing FET Sensor ("DG BSS FET Sensor").

"S/D" refers to the source/drain junctions that form two of the four terminals of a FET.

The expression "high-k" refers to a high dielectric constant. In the field of semiconductor device structures and manufacturing processes, high-k refers to a dielectric constant that is greater than the dielectric constant of $SiO_2$ (i.e., greater than 3.9).

The term "analysis" generally refers to a process or step involving physical, chemical, biochemical, or biological analysis that includes, but is not limited to, characterization, testing, measurement, optimization, separation, synthesis, addition, filtration, dissolution, or mixing.

The term "assay" generally refers to a process or step involving the analysis of a chemical or a target analyte and includes, but is not limited to, cell-based assays, biochemical assays, high-throughput assays and screening, diagnostic assays, pH determination, nucleic acid hybridization assays, polymerase activity assays, nucleic acid and protein sequencing, immunoassays (e.g., antibody-antigen binding assays, ELISAs, and iqPCR), bisulfite methylation assays for detecting methylation pattern of genes, protein assays, protein binding assays (e.g., protein-protein, protein-nucleic acid, and protein-ligand binding assays), enzymatic assays, coupled enzymatic assays, kinetic measurements (e.g., kinetics of protein folding and enzymatic reaction kinetics), enzyme inhibitor and activator screening, chemiluminescence and electrochemiluminescence assays, fluorescent assays, fluorescence polarization and anisotropy assays, absorbance and colorimetric assays (e.g., Bradford assay, Lowry assay, Hartree-Lowry assay, Biuret assay, and BCA assay), chemical assays (e.g., for the detection of environmental pollutants and contaminants, nanoparticles, or polymers), and drug discovery assays. The apparatus, systems, and methods described herein may use or adopt one or more of these assays to be used with any of the FET Sensor described designs.

The term "liquid biopsy" generally refers to a biopsy sample obtained from a subject's bodily fluid as compared to a subject's tissue sample. The ability to perform assays using a body fluid sample is oftentimes more desirable than using a tissue sample. The less invasive approach using a body fluid sample has wide ranging implications in terms of patient welfare, the ability to conduct longitudinal disease monitoring, and the ability to obtain expression profiles even when tissue cells are not easily accessible, e.g., in the prostate gland. Assays used to detect target analytes in liquid biopsy samples include, but are not limited to, those described above. As a non-limiting example, a circulating tumor cell (CTC) assay can be conducted on a liquid biopsy sample.

For example, a capture reagent (e.g., an antibody) immobilized on a FET Sensor may be used for detection of a target analyte (e.g., a tumor cell marker) in a liquid biopsy sample using a CTC assay. CTCs are cells that have shed into the vasculature from a tumor and circulate, e.g., in the bloodstream. Generally CTCs are present in circulation in extremely low concentrations. To assay the CTCs, CTCs are enriched from patient blood or plasma by various techniques known in the art. CTCs may be stained for specific markers using methods known in the art including, but not limited to, cytometry (e.g., flow cytometry)-based methods and IHC-based methods. For the apparatus, systems, and methods described herein, CTCs may be captured or detected using a capture reagent or the nucleic acids, proteins, or other cellular milieu from the CTCs may be targeted as target analytes for binding to or detection by a capture reagent.

When a target analyte is detected on or from a CTC, e.g., an increase in target analyte expressing or containing CTCs may help identify the subject as having a cancer that is likely to respond to a specific therapy (e.g., one associated with a target analyte) or allow for optimization of a therapeutic regimen with, e.g., an antibody to the target analyte. CTC measurement and quantitation can provide information on, e.g., the stage of tumor, response to therapy, disease progression, or a combination thereof. The information obtained from detecting the target analyte on the CTC can be used, e.g., as a prognostic, predictive, or pharmacodynamic biomarker. In addition, CTCs assays for a liquid biopsy sample may be used either alone or in combination with additional tumor marker analysis of solid biopsy samples.

The term "identification" generally refers to the process of determining the identity of a target analyte based on its binding to a capture reagent whose identity is known.

The term "measurement" generally refers to the process of determining the amount, quantity, quality, or property of a target analyte based on its binding to a capture reagent.

The term "quantitation" generally refers to the process of determining the quantity or concentration of a target analyte based on its binding to a capture reagent.

The term "detection" generally refers to the process of determining the presence or absence of a target analyte based on its binding to a capture reagent. Detection includes but is not limited to identification, measurement, and quantitation.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid any one of which may exist in the solid, liquid, or gaseous state, and which is typically the subject of an analysis.

The term "reaction" refers to a physical, chemical, biochemical, or biological transformation that involves at least one chemical and that generally involves (in the case of chemical, biochemical, and biological transformations) the breaking or formation of one or more bonds such as covalent, noncovalent, van der Waals, hydrogen, or ionic bonds. The term includes typical chemical reactions such as synthesis reactions, neutralization reactions, decomposition reactions, displacement reactions, reduction-oxidation reactions, precipitation, crystallization, combustion reactions, and polymerization reactions, as well as covalent and non-covalent binding, phase change, color change, phase formation, crystallization, dissolution, light emission, changes of light absorption or emissive properties, temperature change or heat absorption or emission, conformational change, and folding or unfolding of a macromolecule such as a protein.

"Capture reagent" as used herein, is a molecule or compound capable of binding the target analyte or target reagent, which can be directly or indirectly attached to a substantially solid material. The capture agent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte" as used herein, is the substance to be detected in the test sample using the present invention. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Test sample" as used herein, means the composition, solution, substance, gas, or liquid containing the target analyte to be detected and assayed using the present invention. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to naturally-occurring and non-naturally occurring samples or combinations thereof. Naturally-occurring test samples can be synthetic or synthesized. Naturally-occurring test samples include body or bodily fluids isolated from anywhere in or on the body of a subject, including but not limited to, blood, plasma, serum, urine, saliva or sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof, and environmental samples such as ground water or waste water, soil extracts, air, and pesticide residues or food-related samples.

Detected substances can include, e.g., nucleic acids (including DNA and RNA), hormones, different pathogens (including a biological agent that causes disease or illness to its host, such as a virus (e.g., H7N9 or HIV), a protozoan (e.g., Plasmodium-causing malaria), or a bacteria (e.g., *E. coli* or *Mycobacterium tuberculosis*)), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include but are not limited to, e.g., pH changes, lactose changes, changing concentration, particles per unit time where a fluid flows over the device for a period of time to detect particles, e.g., particles that are sparse, and other parameters.

As used herein, the term "immobilized," when used with respect to, e.g., a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based upon the properties of the substrate surface, the medium carrying the capture reagent, and the properties of the capture reagent In some cases, a substrate surface may be first modified to have functional groups bound to the surface. The functional groups may then bind to biomolecules or biological or chemical substances to immobilize them thereon.

The term "nucleic acid" generally refers to a set of nucleotides connected to each other via phosphodiester bond and refers to a naturally occurring nucleic acid to which a naturally occurring nucleotide existing in nature is connected, such as DNA comprising deoxyribonucleotides having any of adenine, guanine, cytosine, and thymine connected to each other and/or RNA comprising ribonucleotides having any of adenine, guanine, cytosine, and uracil connected to each other. In addition, non-naturally occurring nucleotides and non-naturally occurring nucleic acids are within the scope of the nucleic acid of the present invention. Examples include peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA. Nucleic acids include those that may be modified. For example, a phosphoric acid group, a sugar, and/or a base in a nucleic acid may be labeled as necessary. Any substances for nucleic acid labeling known in the art can be used for labeling. Examples thereof include but are not limited to radioactive isotopes (e.g., 32P, 3H, and 14C), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

Aptamer as used herein refers to oligonucleic acids or peptide molecules that bind to a specific target molecule. The concept of using single-stranded nucleic acids (aptamers) as affinity molecules for protein binding was initially disclosed in 1990 (Ellington and Szostak 1990, 1992; Tuerk and Gold 1990), and is based on the ability of short sequences to fold, in the presence of a target, into unique, three-dimensional structures that bind the target with high affinity and specificity. Eugene W. M Ng et al., 2006, discloses that aptamers are oligonucleotide ligands that are selected for high-affinity binding to molecular targets.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The three CDRs constitute about 15-20% of the variable domains. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. (Kuby, Immunology, 4th ed., Chapter 4. W.H. Freeman & Co., New York, 2000).

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

The term "polymer" means any substance or compound that is composed of two or more building blocks ('mers') that are repetitively linked to each other. For example, a "dimer" is a compound in which two building blocks have been joined together. Polymers include both condensation and addition polymers. Typical examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

Overview of Biosensing Cartridge

FIG. 1 illustrates an overview of various components that are integrated together to form an exemplary biosensing cartridge 102. Biosensing cartridge 102 may include a plurality of fluidic channels that are configured to control fluid flow both towards and away from a sensing location where the presence of a target analyte can be detected.

In this illustrative embodiment, biosensing cartridge 102 includes an array of FET Sensors 104. FET Sensors 104 make up the transducer component of biosensing cartridge 102. FET Sensors 104 may be arranged in an array and individually addressed to detect binding events at the surface of the FET Sensor sensing layer. In one embodiment, FET Sensors 104 include dual gate back-side FET Sensors. In alternative embodiments other types of FET Sensor-based sensors may be used.

Biosensing cartridge 102 includes a biological interface 106. Biological interface 106 may be coupled to dual gate back-side sensing FET Sensors 104 to facilitate binding reactions at the surface of dual gate back-side sensing FET Sensors 104, which can be then be detected. Various types of biomolecules may form a part of biological interface 106, such as DNA or RNA aptamers and antibodies, to name a few examples. Further details regarding the biological interface, and its associated chemistry and biology mechanics, will be discussed in detail herein.

Biosensing cartridge 102 includes various levels of chip packaging 108 in order to integrate a dual gate back-side sensing FET Sensor chip into a fluidic environment. Biosensing cartridge 102 also includes a fluidic component 110 having microfluidic channels to manage delivery of liquids to FET Sensors 104. Fluidic component 110 also incorporates fluidic inlets for interfacing with fluids that are delivered from outside of biosensing cartridge 102.

The integration of various components in biosensing cartridge 102 yields a compact and portable platform that can be used for a multitude of various biosensing applications. The use of FET Sensors with the integrated fluidics component produces accurate results while using low sample volumes. Additionally, biosensing cartridge 102 may be configured to be operated in a fully autonomous way by an analyzer, and then disposed of after use.

The description herein is split into four major sections to describe components of biosensing cartridge 102 in further detail. The first section will describe the arrangement and fabrication of dual gate back-side bioFET sensors 104. The second section will describe the packaging process. The third section will describe fluidic component 110, and further describe the interaction between biosensing cartridge 102 and an analyzer. The final section will provides details regarding the biology and the various biosensing applications using dual gate back-side FET Sensors 104.

Dual Gate Back-Side FET Sensors

Dual gate back-side FET Sensors utilize semiconductor manufacturing techniques and biological capture reagents to form sensitive and easily arrayed sensors. While conventional MOSFETs have a single gate electrode that is connected to a single electrical node, the dual gate back-side sensing FET Sensor has two gate electrodes each of which is connected to a different electrical node. A first one of the two gate electrodes is referred to herein as the front-side gate and the second one of the two gate electrodes is referred to herein as the back-side gate. Both the front-side gate and the back-side gate are configured such that, in operation, each one may be electrically charged and/or discharged and thereby each influences the electric field between the source/drain terminals of the dual gate back-side sensing FET Sensor. The front-side gate is electrically conductive, separated from a channel region by a front-side gate dielectric, and configured to be charged and discharged by an electrical circuit to which it is coupled. The back-side gate is typically separated from the channel region by a back-side gate dielectric, and includes a biofunctionalized sensing layer disposed on the back-side gate dielectric. The amount of electric charge on the back-side gate is a function of whether a biorecognition reaction has occurred. In the typical operation of dual gate back-side sensing FET Sensors, the front-side gate is charged to a voltage within a predetermined range of voltages. The voltage on the front-side gate determines a corresponding conductivity of the FET Sensor's channel region. A relatively small amount of change to the electric charge on the back-side gate changes the conductivity of the channel region. It is this change in conductivity that indicates a biorecognition reaction.

One advantage of FET Sensors is the prospect of label-free operation. Specifically, FET Sensors enable the avoidance of costly and time-consuming labeling operations such as the labeling of an analyte with, for instance, fluorescent or radioactive probes.

Figure 2:
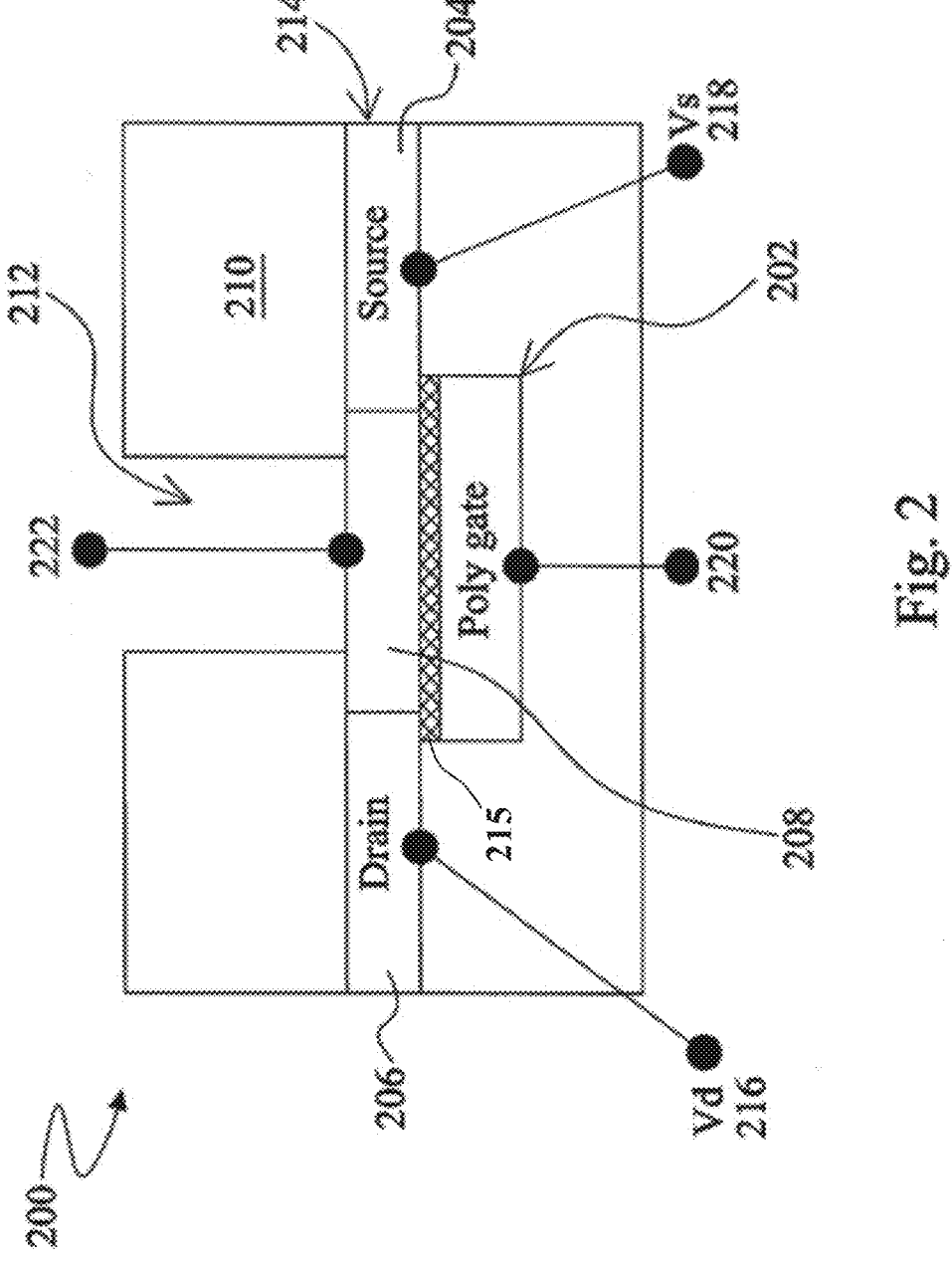
FIG. 2 is a cross-sectional view of an exemplary dual-gate back-side sensing FET Sensor.

Referring to FIG. 2, illustrated is an exemplary dual gate back-side sensing FET sensor 200. Dual gate back-side sensing FET sensor 200 includes a control gate 202 formed over substrate 214 and separated therefrom by an intervening dielectric 215 disposed on substrate 214. Substrate 214 further includes a source region 204, a drain region 206, and a channel region 208 between source region 204 and drain region 206. In an embodiment, substrate 214 has a thickness between about 100 nm and about 130 nm. Gate 202, source region 204, drain region 206, and channel region 208 may be formed using suitable CMOS process technology. Gate 202, source region 204, drain region 206, and channel region 208 form a FET. An isolation layer 210 is disposed on the opposing side of substrate 214 from gate 202. In one embodiment, isolation layer 210 has a thickness of about 1 μm. In this disclosure the side of substrate 214 over which gate 202 is disposed is referred to as the "front-side" of substrate 214. Similarly, the side of substrate 214 on which isolation layer 210 is disposed is referred to as the "back-side."

An opening 212 is provided in isolation layer 210. Opening 212 may be substantially aligned with gate 202. In other embodiments, opening 212 is larger than gate 202 and may extend over multiple dual gate back-side sensing FET Sensors. An interface layer (not shown) may be disposed in opening 212 on the surface of channel region 208. The interface layer may be operable to provide an interface for positioning and immobilizing one or more receptors for detection of biomolecules or bio-entities. Further details regarding the interface layer are provided herein.

Dual gate back-side sensing FET sensor 200 includes electrical contacts to drain region 206 (Vd 216), source region 204 (Vs 218), gate structure 202 (front-side gate 220), and/or active region 208 (e.g., back-side gate 222). It should be noted that back-side gate 222 does not need to physically contact substrate 214 or any interface layer over substrate 214. Thus, while a conventional FET uses a gate contact to control conductance of the semiconductor between the source and drain (e.g., the channel), dual gate back-side sensing FET sensor 200 allows receptors formed on the opposing side of the FET device to control the conductance, while gate structure 202 provides another gate to control the conductance. Therefore, dual gate back-side sensing FET sensor 200 may be used to detect one or more specific biomolecules or bio-entities in the environment around and/or in opening 212, as discussed in more detail using various examples herein.

Dual gate back-side sensing FET sensor 200 may be connected to additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), high voltage transistors, and/or high frequency transistors; other suitable components; and/or combinations thereof. It is further understood that additional features can be added in dual gate back-side sensing FET sensor 200, and some of the features described can be replaced or eliminated, for additional embodiments of dual gate back-side sensing FET sensor 200. Further details regarding example fabrication procedures of dual gate back-side sensing FET sensor 200 may be found in co-owned U.S. Patent Publication No. 2013/0200438 and U.S. Patent Publication No. 2014/0252421.

Figure 3:
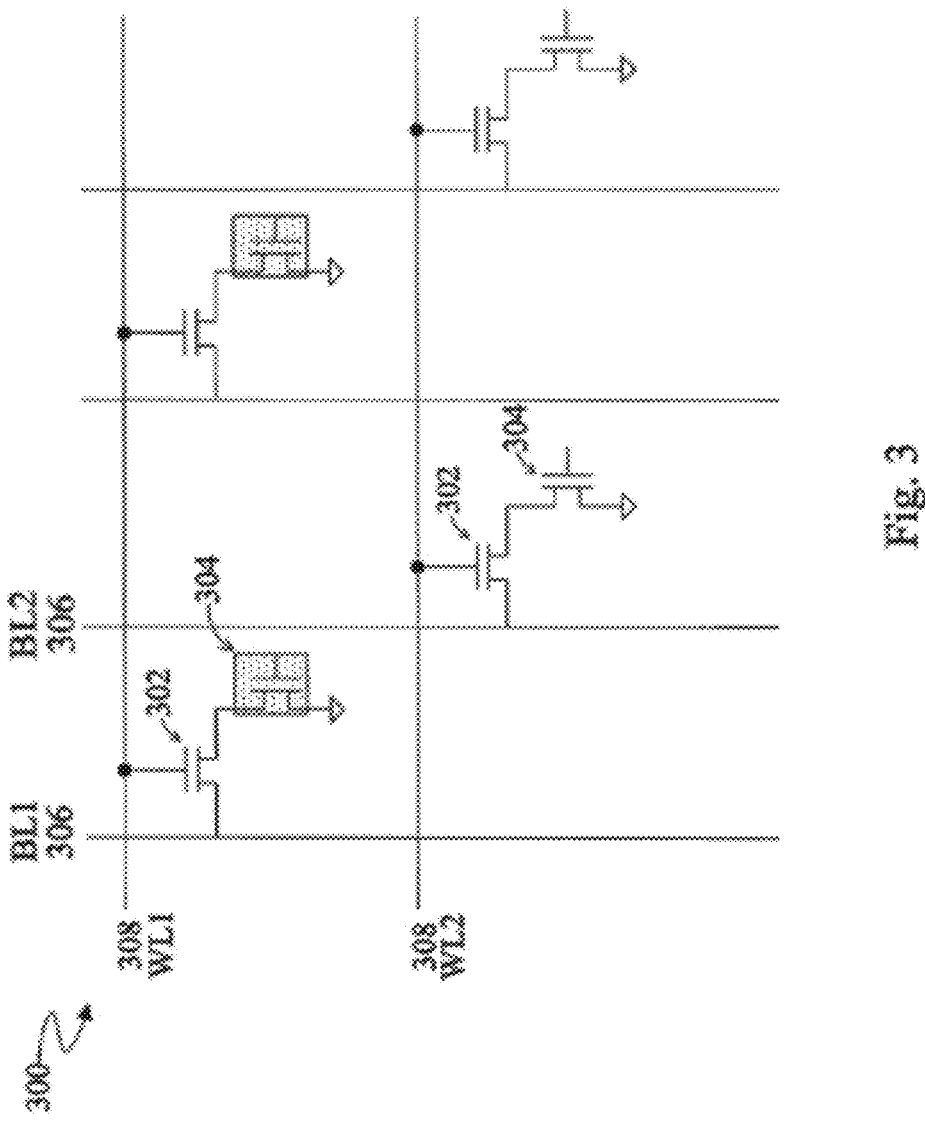
FIG. 3 is a circuit diagram of a plurality of FET Sensors configured in an exemplary addressable array.

Referring to FIG. 3, illustrated is a schematic of an exemplary addressable array 300 of FET Sensors 304 connected to bit lines 306 and word lines 308. It is noted that the terms bit lines and word lines are used herein to indicate similarities to array construction in memory devices, however, there is no implication that memory devices or a storage array necessarily be included in the array. Addressable array 300 may have similarities to that employed in other semiconductor devices such as dynamic random access memory (DRAM) arrays. For example, dual gate back-side sensing FET Sensor 200, described above with reference to FIG. 2, may be formed in a position that a capacitor would be found in a DRAM array. Schematic 300 is exemplary only and one would recognize other configurations are possible.

FET Sensors 304 may each be substantially similar to dual gate back-side sensing FET Sensor 200. FETs 302 are configured to provide connection between a drain terminal of FET Sensor 304 and bit line 306. In this way FETs 302 are analogous to access transistors in a DRAM array. In this exemplary embodiment, FET Sensors 304 is a dual gate back-side sensing FET Sensor and includes a sensing gate provided by a receptor material disposed on a dielectric layer overlying a FET active region disposed at a reaction site, and a control gate provided by a gate electrode (e.g., polysilicon) disposed on a dielectric layer overlying the FET active region.

Schematic 300 shows an array formation that may be advantageous in detecting small signal changes provided by minimal biomolecules or bio-entities introduced to FET Sensors 304. The arrayed format using bit lines 306 and word lines 308 allows for a decreased number of input/output pads. Amplifiers may be used to enhance the signal strength to improve the detection ability of the device having the circuit arrangement of schematic 300. In an embodiment, when particular word lines 308 and bit lines 306 are asserted, the corresponding access transistors 302 will be turned on (e.g., like a switch.) When the gate of the associated FET Sensor 304 (e.g., such as back-side gate 222 of the dual gate back-side sensing FET sensor 200) has its charge affected by the bio-molecule presence, FET Sensor 304 will transfer electrons and induce the field effect charging of the device, thereby modulating the current (e.g., Ids). The change of the current (e.g., Ids) or threshold voltage (Vt) can serve to indicate detection of the relevant biomolecules or bio-entities. Thus, the device having schematic 300 can achieve a biosensor application including application with differential sensing for enhanced sensitivity.

Figure 4:
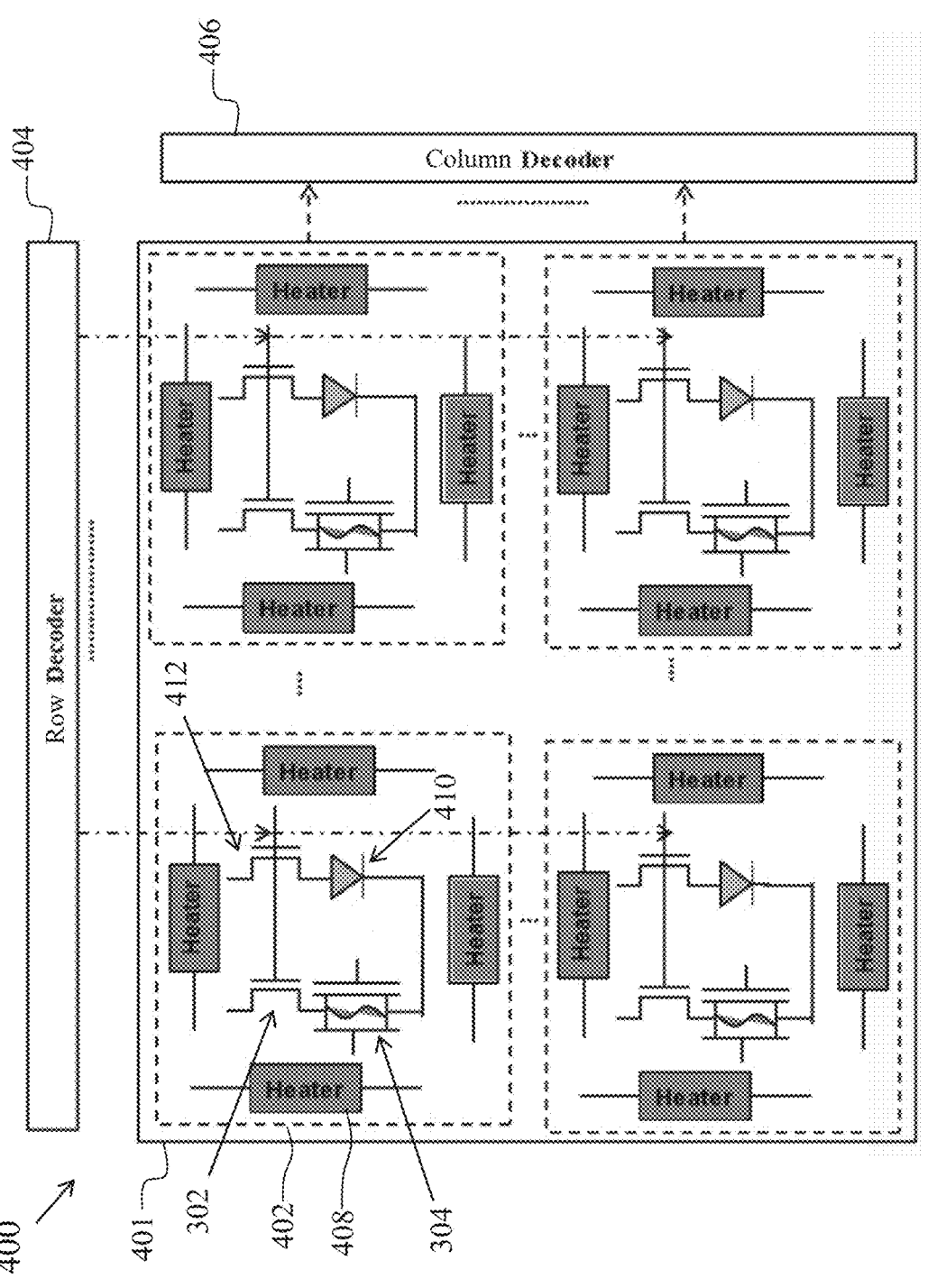
FIG. 4 is a circuit diagram of an exemplary addressable array of dual gate FET Sensors and heaters.

Referring to FIG. 4, an exemplary layout 400 is presented. Exemplary layout 400 includes access transistor 302 and FET Sensor 304 arranged as an array 401 of individually addressable pixels 402. Array 401 may include any number of pixels 402. For example, array 401 may include 128×128 pixels. Other arrangements may include 256×256 pixels or non-square arrays such as 128×256 pixels.

Each pixel 402 includes access transistor 302 and dual gate back-side sensing FET Sensor 304 along with other components that may include one or more heaters 408 and a temperature sensor 410. In this example, access transistor 302 is an n-channel FET. An n-channel FET 412 may also act as an access transistor for temperature sensor 410. In this illustrative example, the gates of FETs 302 and 412 are coupled in common, though this is not required. Each pixel 402 (and its associated components) may be individually addressed using column decoder 404 and row decoder 406. In one example, each pixel 402 has a size of about 10 micrometers by about 10 micrometers. In another example, each pixel 402 has a size of about 5 micrometers by about 5 micrometers, or has a size of about 2 micrometers by about 2 micrometers.

Column decoder 406 and row decoder 404 may be used to determine the ON/OFF state of n-channel FETs 302 and 412. Turning on n-channel FET 302 provides a current to an S/D region of dual gate back-side sensing FET Sensor 304. When these devices are ON, a current Ids flows through FET Sensor 304 and may be measured.

Heater 408 may be used to locally increase a temperature around a dual gate back-side sensing FET Sensor 304. Heater 408 may be constructed using any known technique, such as forming a metal pattern with a high current running through it. Heater 408 may also be a thermoelectric heater/cooler, like a Peltier device. Heater 408 may be used during certain biological tests, such as to denature DNA or RNA, or to provide a more ideal binding environment for certain biomolecules. Temperature sensor 410 may be used to measure the local temperature around dual gate back-side sensing FET Sensor 304. In one embodiment, a control loop may be created to control the temperature using heater 408 and the feedback received from temperature sensor 410. In another embodiment, heater 408 may be a thermoelectric heater/cooler that allows for local active cooling of the components within pixel 402.

Figure 5:
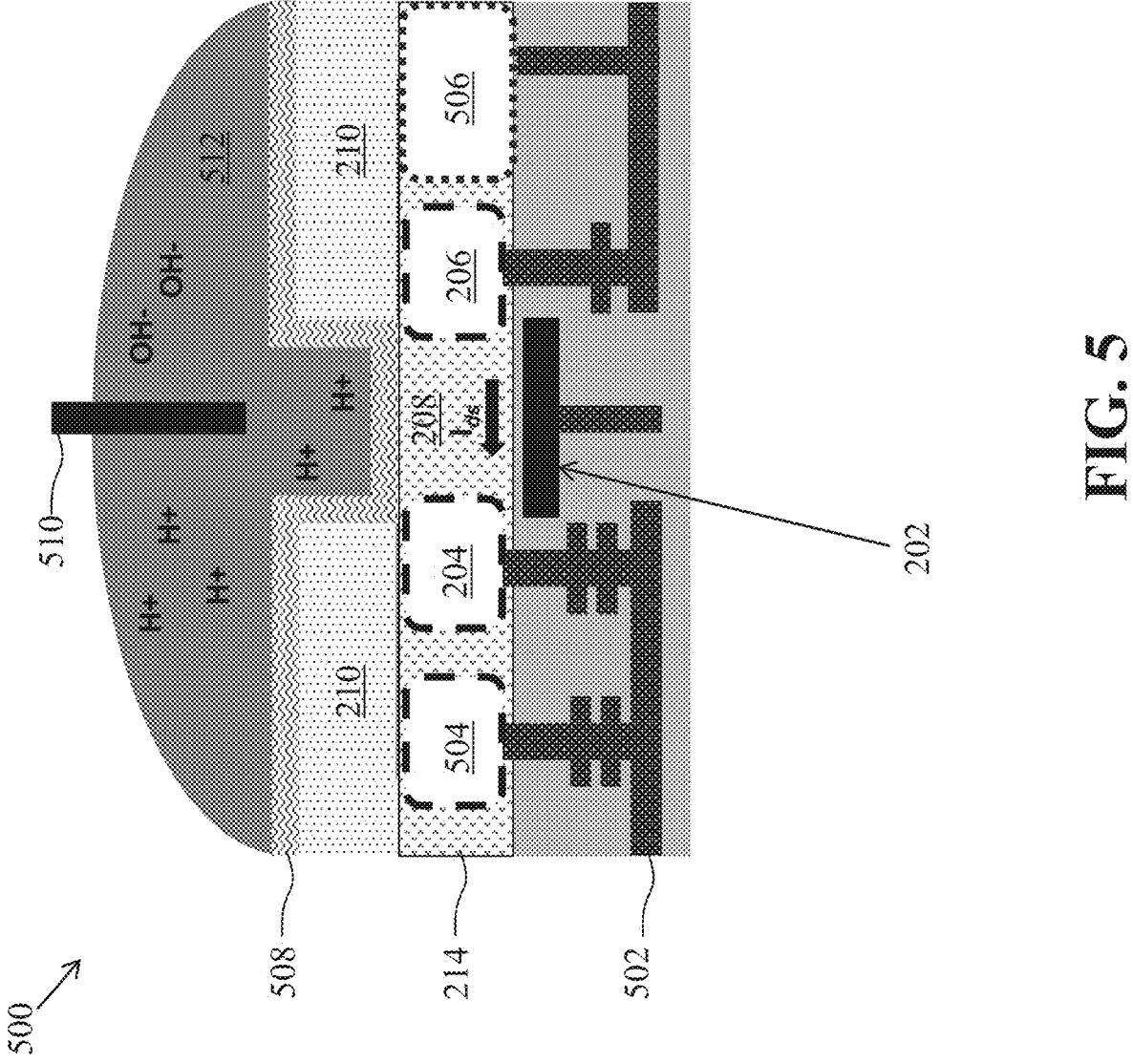
FIG. 5 is a cross-sectional view of an exemplary dual gate back-side sensing FET Sensor configured as a pH sensor.

Referring to FIG. 5, a cross section of an example dual gate back-side sensing FET Sensor 500 is provided. The dual gate back-side sensing FET Sensor 500 is one implementation of dual gate back-side sensing FET Sensor 200, thus previously described elements from FIG. 2 are labeled with element numbers from FIG. 2 and their descriptions are not repeated here. Dual gate back-side sensing FET Sensor 500 includes gate 202, source region 204, drain region 206, and channel region 208, where source region 204 and drain region 206 are formed within substrate 214. Gate 202, source region 204, drain region 206, and channel region 208 form a FET. It should be noted that the various components of FIG. 5 are not intended to be drawn to scale and are exaggerated for visual convenience, as would be understood by a person skilled in the relevant art.

In an exemplary embodiment, dual gate back-side sensing FET Sensor 500 is coupled to various layers of metal interconnects 502 that make electrical connection with the various doped regions and other devices formed within substrate 214. Metal interconnects 502 may be manufactured using fabrication processes well known to a person skilled in the relevant art.

Dual gate back-side FET Sensor 500 may include a body region 504 separate from source region 204 and drain region 206. Body region 504 may be used to bias the carrier concentration in active region 208 between source region 204 and drain region 206. As such, a negative voltage bias may be applied to body region 504 to improve the sensitivity of dual gate back-side FET Sensor 500. In one embodiment, body region 504 is electrically connected with source region 204. In another embodiment, body region 504 is electrically grounded.

Dual gate back-side FET Sensor 500 may be coupled to additional circuitry 506 fabricated within substrate 214. Circuitry 506 may include any number of MOSFET devices, resistors, capacitors, or inductors to form circuitry to aid in the operation of dual gate back-side sensing FET Sensor 500. For example, column decoder 406 and row decoder 404 may be formed in circuitry 506. Circuitry 506 may include any amplifiers, analog to digital converters (ADCs), digital to analog converters (DACs), voltage generators, logic circuitry and DRAM memory, to name a few examples. All or some of the components of additional circuitry 506 may be integrated in the same substrate 214 as dual gate back-side FET Sensor 500. It should be understood that many FET sensors, each substantially similar to dual gate back-side FET Sensor 500, may be integrated on substrate 214 and coupled to additional circuitry 506. In another example, all or some of the components of additional circuitry 506 are provided on another semiconductor substrate separate from substrate 214. In yet another example, some components of additional circuitry 506 are integrated in the same substrate 214 as dual gate back-side FET Sensor 500, and some components of additional circuitry 506 are provided on another semiconductor substrate separate from substrate 214.

Still referring to the illustrative example of FIG. 5, dual gate back-side sensing FET Sensor 500 includes an interface layer 508 deposited over isolation layer 210 and within the opening over channel region 208. In one embodiment, interface layer 508 has a thickness between about 20 Å and about 40 Å. Interface layer 508 may be a high-K dielectric material, such as hafnium silicate, hafnium oxide, zirconium oxide, aluminum oxide, tantalum pentoxide, hafnium dioxide-alumina ($HfO_2$—$Al_2O_3$) alloy, or any combinations thereof. Interface layer 508 may act as a support for the attachment of capture reagents as will be discussed in more detail later in the section directed to biological sensing.

An example operation of dual gate back-side FET Sensor 500 acting as a pH sensor will now be described. Briefly, a fluid gate 510 is used to provide the electrical contact to the "second gate" of the dual gate back-side sensing FET Sensor. A solution 512 having a given pH is provided over the reaction site of dual gate back-side sensing FET Sensor 500, and fluid gate 510 is placed within solution 512. The pH of the solution is generally related to the concentration of hydrogen ions [$H^+$] in the solution. The accumulation of the ions near the surface of interface layer 508 above channel region 208 will affect the formation of the inversion layer within channel region 208 that forms the conductive pathway between source region 204 and drain region 206. This can be measured by the change in the conductivity of the FET Sensor. In one embodiment, fluid gate 510 is used as the gate of the transistor during sensing while gate 202 remains floating. In another embodiment, fluid gate 510 is used as the gate of the transistor during sensing while gate 202 is biased at a given potential. For example, gate 202 may be biased at a potential between –2V and 2V depending on the application, while fluid gate 510 is swept between a range of voltages. In another embodiment, fluid gate 510 is biased at a given potential (or grounded) while gate 202 is used as the gate of the transistor (e.g., its voltage is swept across a range of potentials) during sensing. Fluid gate 510 may be formed from platinum or may be formed from any other commonly used material(s) for reference electrodes in electrochemical analysis. The most common reference electrode is the Ag/AgCl electrode, having a stable potential value of about 0.230 V.

Figures 6A, 6B:
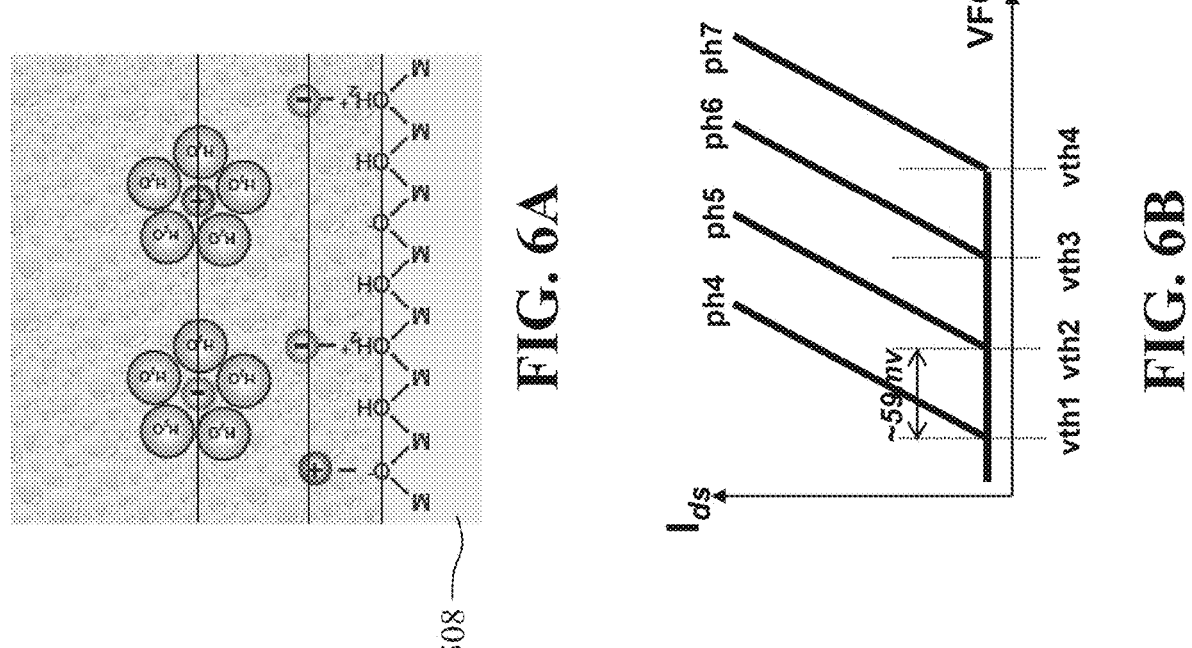
FIG. 6A illustrates an example of the binding of ions to a receptor layer.
FIG. 6B illustrates a change in threshold voltage in an exemplary FET Sensor based on pH.

FIG. 6A shows ions in solution binding to a surface of interface layer 508. A top-most atomic layer of interface layer 508 is depicted as the various dangling [$O^-$], [OH], and [$OH_2^+$] bonds. As the ions accumulate on the surface, the total surface charge affects the threshold voltage of the transistor. As used herein, the threshold voltage is the minimum potential between the gate and the source of a FET Sensor that is required to form a conductive path of minority carriers between the source and the drain of the FET sensor. The total charge also directly relates to pH of the solution, as a higher accumulation of positive charge signifies a low pH while a higher accumulation of negative charge signifies a high pH. FIG. 6B illustrates the change in threshold voltage that results due to different pH values in an n-channel FET Sensor. As can be observed in the figure, a 59 mV increase in threshold voltage roughly signifies an increase of one in the pH of the solution. In other words, one pH change results in total surface charge equivalent of 59 mV when measured as the voltage required to turn on the transistor.

Chip Packaging

Figure 7:
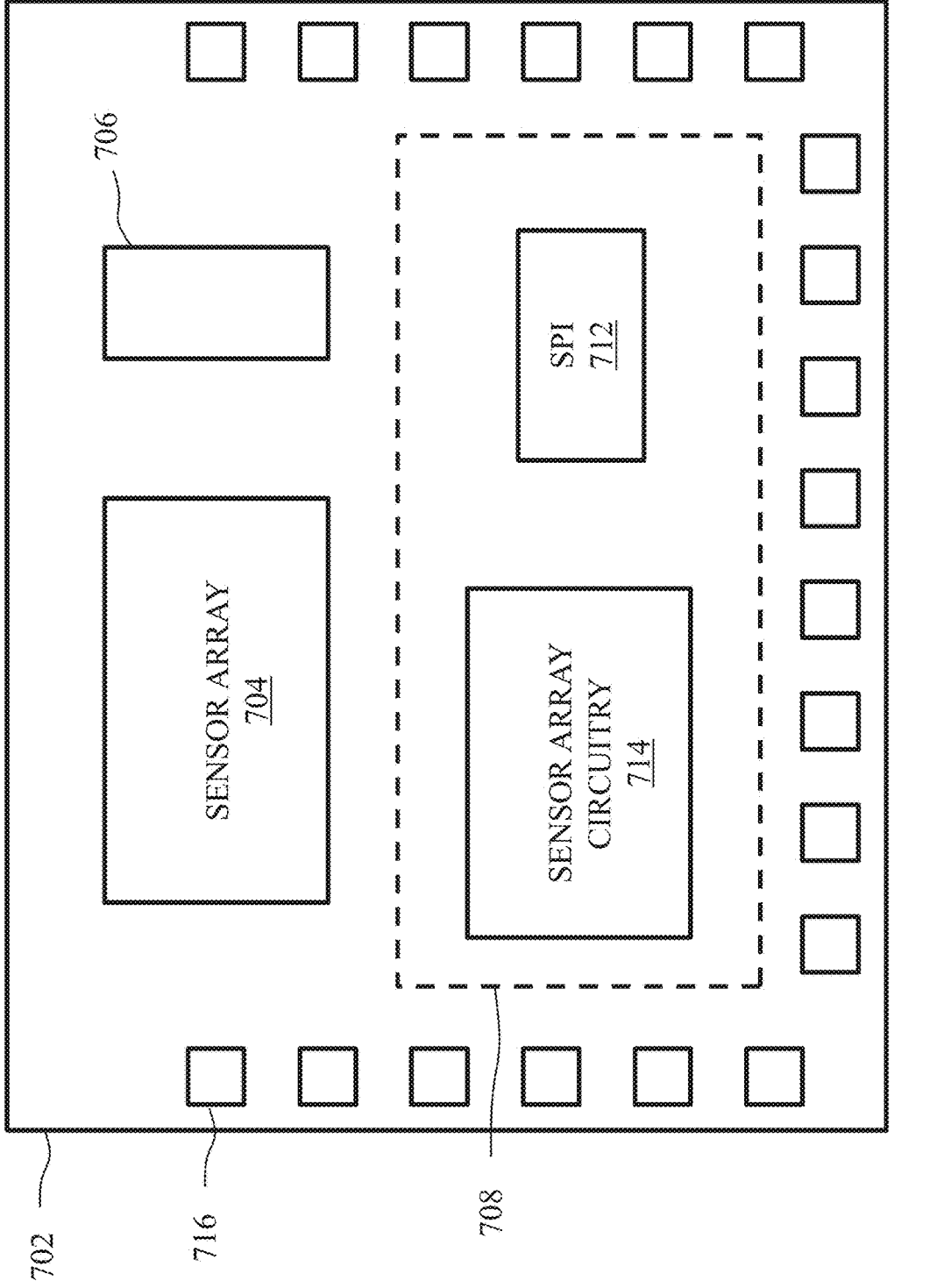
FIG. 7 is a floor plan diagram of an exemplary biosensor chip.

Referring to FIG. 7, an exemplary floor plan for a semiconductor chip 702 is shown. Chip 702 includes sensor array 704, an optional reference electrode 706, analog circuitry 708, and I/O pads 716. Chip 702 may be silicon, gallium arsenide, or indium phosphide to name a few examples. Chip 702 may have dimensions of about 3 mm by about 2.5 mm.

Sensor array 704 represents the array of dual gate backside sensing FET Sensors such as those illustrated above in FIGS. 2 and 5. The array may be arranged as a row-column matrix of pixels as illustrated, for example, in FIG. 4. The various FET Sensors in sensor array 704 may be functionalized with the same or different capture reagents to perform biosensing for various analytes.

Reference electrode 706 may be patterned on the same chip 702 that includes sensor array 704. Reference electrode 706 may be roughly aligned with sensor array 704 along an X or Y direction, such that a fluidic channel may be placed over both sensor array 704 and reference electrode 706. In another embodiment, reference electrode 706 is provided elsewhere off of chip 702.

Reference electrode 706 may comprise any material having a relatively stable potential. Example reference electrode materials include platinum or Ag/AgCl. Fabricating an Ag/AgCl electrode on a substrate surface is well known in the art as described, for example, by Moschou et al., "Surface and Electrical Characterization of Ag/AgCl Pseudo-Reference Electrodes Manufactured with Commercially Available PCB Technologies," Sensors, vol. 15(8), 2015, pp. 18102-18113.

Analog circuitry 708 may include circuitry related to the operation of sensor array 704. As such, analog circuitry 708 may be configured to provide signals to, and measure signals from, sensor array 704, while interfacing with various I/O pads 716. In one embodiment, analog circuitry 708 includes a serial peripheral interface (SPI) 712, and sensor array circuitry 714. In this embodiment, a spacing between sensor array 704 and sensor array circuitry 714 is no shorter than about 135 micrometers.

SPI 712 may be a serial interface circuit to facilitate data transmission between sensor array circuitry 714 and an analyzer unit described in more detail below. The general operation of a SPI would be well understood to a person skilled in the relevant art. Sensor array circuitry 714 may include any number of reference voltage generators, operational amplifiers, low pass filters, ADCs, and DACs to provide signals to, and receive signals from, sensor array 704.

In one example, a biasing reference voltage may be generated using sensor array circuitry 714 to provide a negative voltage bias around −0.24 volts to the body region of a given FET Sensor or set of FET Sensors in sensor array 704. A tunable voltage may also be provided to the fluid gate of a given FET Sensor or set of FET Sensors in sensor array 704 when performing the sensing.

When measuring signals (such as Ids) received from a given FET Sensor or a set of FET Sensors in sensor array 704, sensor array circuitry 714 may receive the measured signals and pass them through a trans-impedance amplifier, i.e., a current-to-voltage converter, followed by one or more additional amplification stages, low pass filters, and ultimately an ADC, before the resulting signal is output to an I/O pad 716. Noise may also be reduced from the measured signal by subtracting a background AC signal from the measured signal before the measured signal is amplified. A temperature signal (received from one or more temperature sensors in sensor array 704) may also be amplified, filtered, and passed through an ADC before being output to an I/O pad 716.

In various embodiments a plurality of I/O pads 716 may be patterned along the periphery of chip 702. Many more I/O pads may be provided than actual inputs and outputs used by the various components of chip 702. In one embodiment, wire bonding techniques may be used to couple various I/O pads 716 to another substrate or package bonded to chip 702. In one particular embodiment, 32 I/O pads may be patterned around the periphery of chip 702. The size of a given I/O pad 716 may be about 80 micrometers by about 70 micrometers, and the pitch between I/O pads 716 may be about 150 micrometers. A spacing between sensor array 704 and a closest I/O pad 716 may be no shorter than about 400 micrometers while a spacing between I/O pads 716 and an outermost edge of chip 702 may be no shorter than about 177.5 micrometers.

Figure 8:
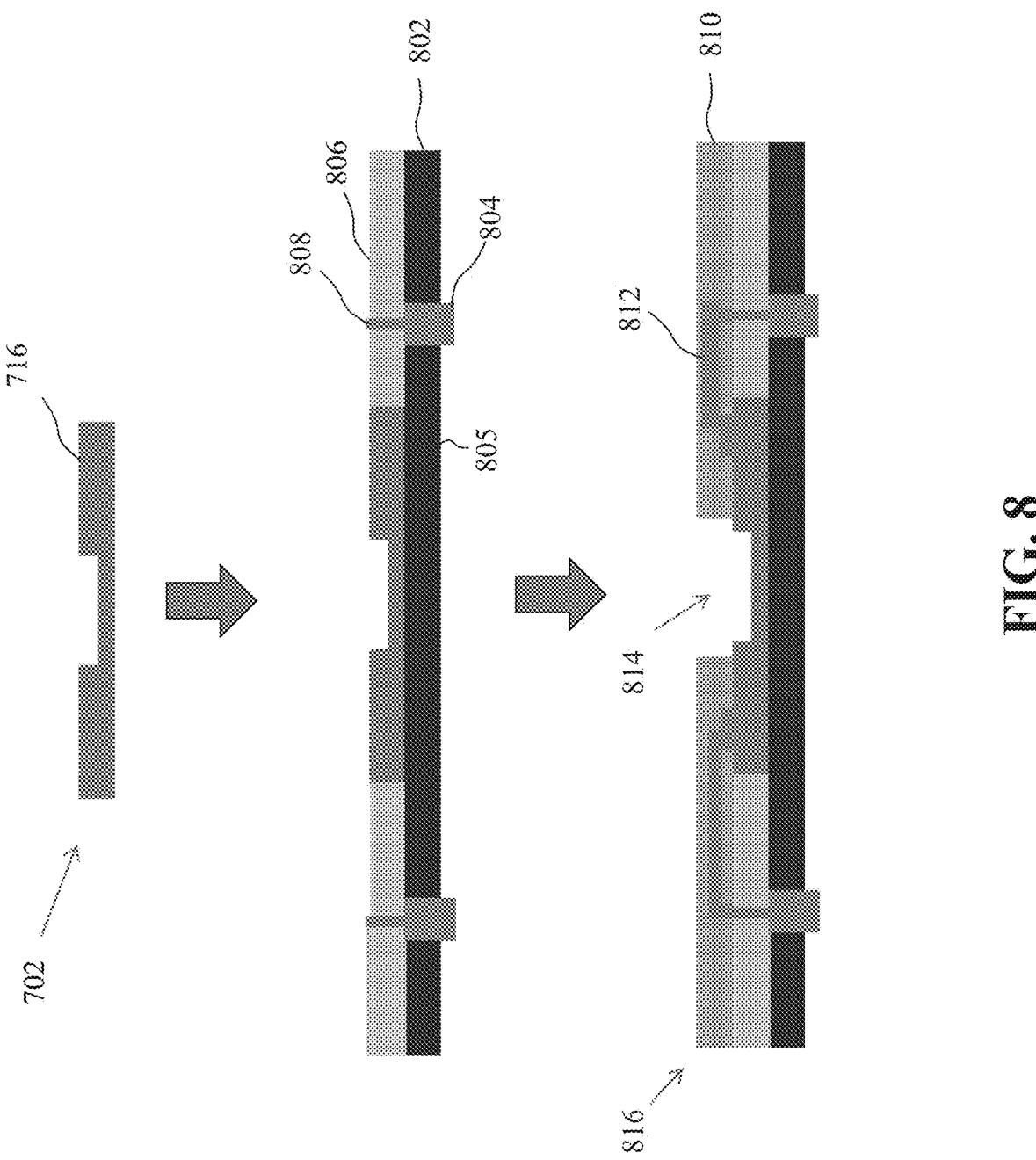
FIG. 8 shows a series of cross-sectional views illustrating a fabrication process for mounting an exemplary biosensor chip to a handle layer.

Referring to FIG. 8, an exemplary packaging scheme is illustrated for chip 702. Chip 702 with its I/O pads 716 is bonded to a carrier layer 802. Carrier layer 802 may be another semiconductor substrate, such as a silicon substrate. In another example, carrier layer 802 is an insulator, such as a hard plastic material. Chip 702 may be bound to carrier layer 802 using any known binding techniques, such as by using solder or an adhesive.

In one embodiment, carrier layer 802 includes a plurality of through-holes filled with a conductive material 804. Conductive material 804 may be any metal such as, but not limited to, tin, copper, aluminum, gold, or any alloy thereof. Conductive material 804 may include a solder bump or solder ball at a bottom surface 805 of carrier layer 802. The solder may extend beyond surface 805.

The chip package also includes a first insulating layer 806 that abuts the sides of chip 702, according to an embodiment. First insulating layer 806 may also be a plastic material or resin that fills the areas around chip 702 and can aid in securing chip 702 in place. In an exemplary embodiment, first insulating layer 806 includes through-holes that are also filled with conductive plugs 808. Conductive plug 808 may be the same material as conductive material 804. Conductive plugs 808 are substantially aligned over corresponding areas of conductive material 804 such that an ohmic contact is formed between conductive plugs 808 and conductive material 804.

Once chip 702 has been secured to carrier layer 802, and has first insulating layer 806 around it, electrical connections 812 may be made between I/O pads 716 and conductive plugs 808. Electrical connections 812 may be formed using wire-bonding techniques as would be understood to a person skilled in the relevant art. In another example, electrical connections 812 are formed using lithographic patterning techniques to pattern a conductive trace to electrically connect I/O pads 716 with corresponding conductive plugs 808. Once electrical connections 812 are formed, a second insulating layer 810 may be deposited to protect electrical connections 812 from the environment. Second insulating layer 810 may be the same material as first insulating layer 806. Second insulating layer 810 may be a resin material that flows around electrical connections 812 and then hardens to form a protective shell. An opening 814 is formed within second insulating layer 810 to create a pathway towards the sensor array present on chip 702. In an embodiment where a reference electrode is also patterned on chip 702, then opening 814 would create a pathway towards the sensor array and the reference electrode.

A final chip package 816 includes chip 702 bound to carrier layer 802 and electrically connected to various conductive solder points or metal pads on bottom surface 805 of carrier layer 802. Chip 702 is also protected from the environment via first insulating layer 806 and second insulating layer 810. Chip package 816 may be more easily handled and coupled to a larger substrate, such as a printed circuit board (PCB). In some embodiments, chip package 816 may be coupled to one or more heat sinks to provide a more efficient heat dissipation path from chip 702 into either the surrounding air or into whatever substrate chip package 816 is attached to. In other embodiments, chip package 816 may be coupled to a Peltier device to provide thermoelectric heating and/or cooling.

Figure 9:
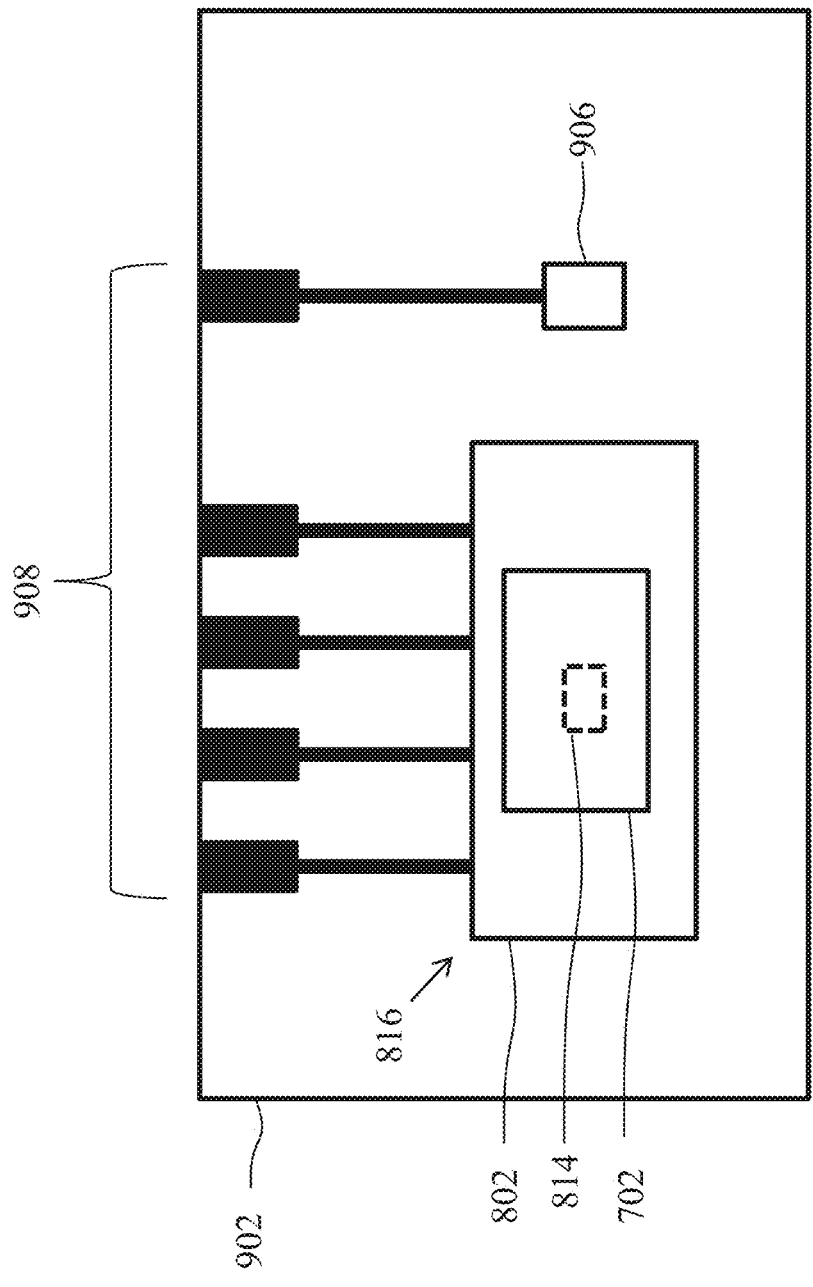
FIG. 9 is a top view of the handle layer having the exemplary biosensor chip mounted to a substrate.

Referring to the illustrative embodiment of FIG. 9, chip package 816 is bonded with a substrate 902. Substrate 902 may be a PCB that includes conductive contact pads to make electrical contact with the solder or conductive pads on the bottom surface of carrier layer 802. A flip-chip bonding technique may be performed to bond chip package 816 onto the surface of substrate 902. Briefly, the solder or conductive pads along the bottom surface of carrier layer 802 are aligned to corresponding conductive pads patterned on substrate 902, and are bonded together to physically attach chip package 816 to substrate 902 and to electrically couple the I/O pads from chip 702 to conductive traces present on substrate 902. The conductive traces on substrate 902 may terminate in edge connectors 908.

One or more edge connectors 908 may provide electrical connection to chip 702. One or more other edge connectors 908 may provide electrical connection to a reference electrode 906 patterned on a surface of substrate 902. Using reference electrode 906 may eliminate the need for providing a reference electrode on chip 702. Each of the one or more edge connectors 908 may be patterned using a metal such as, but not limited, copper, gold, or aluminum. Reference electrode 906 may be fabricated using similar techniques as those discussed above for reference electrode 706 on chip 702.

The dimensions of exemplary chip package 816 may be between about one to two centimeters by one to two centimeters or smaller while the dimensions of substrate 902 may be between three to four centimeters by three to four centimeters or smaller.

Opening 814 is illustrated over chip 702, exposing at least the sensor array of chip 702. In an exemplary embodiment, opening 814 is roughly aligned with reference electrode 906 along an X or Y direction, such that a fluidic channel may be placed over both opening 814 and reference electrode 906.

Fluidic Design

Figure 10:
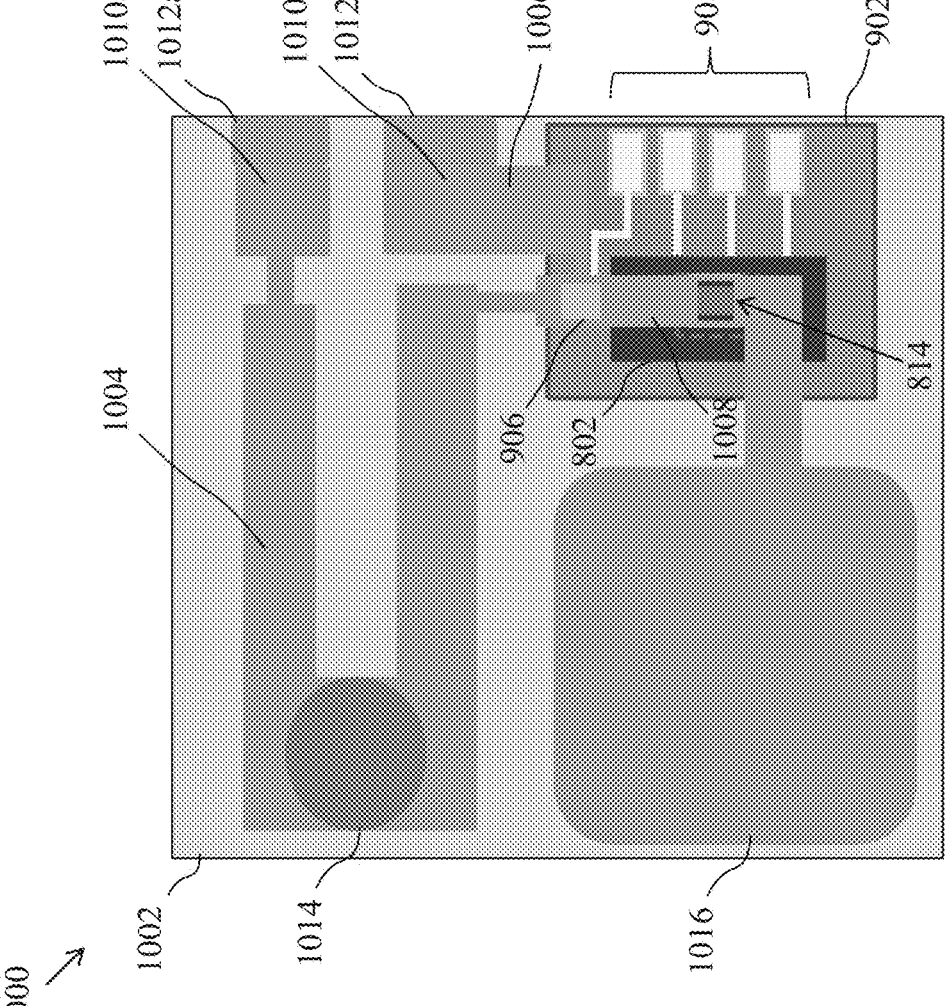
FIG. 10 is a schematic of an exemplary fluidic cartridge having and integrated biosensor chip.

Referring to FIG. 10, a schematic of an exemplary fluidic cartridge 1000 is provided. The schematic illustrates a top-down view of cartridge 1000, and it should be noted that not all elements shown are on the same horizontal plane. Also, the specific dimensions and scale of the various fluidic channels are purposefully not drawn to scale for improved visualization. Cartridge 1000 includes a housing 1002. Housing 1002 may be formed from any plastic material, such as polymethyl methacrylate (PMMA), using injection molding, casting, or 3-D printing techniques, to name a few examples. Housing 1002 may be formed from more than one segment that connects together either mechanically or through the use of an adhesive. In one embodiment, the various fluidic channels and chambers are molded within one or more components of housing 1002. In another embodiment, the various fluidic channels and chambers are formed from a different molded polymer material, such as polydimethylsiloxane (PDMS). The overall dimensions of housing 1002 may be between about 4 centimeters to about 7 centimeters by about 4 centimeters to about 7 centimeters. As technology advances, housing 1002 may become even smaller. In an embodiment, substrate 902 having packaged chip 802 is disposed within housing 1002. In one example, only a portion of substrate 902 is enclosed within housing 1002, while edge connectors 908 are exposed outside of housing 1002.

The fluidic design of exemplary housing 1002 includes at least a first channel 1004, a second channel 1006, and a third channel 1008. Each of first channel 1004 and second channel 1006 includes a corresponding fluid inlet 1010a and 1010b, respectively. The fluid inlets provide areas to inject fluid into cartridge 1000 from outside of cartridge 1000. The fluid inlets may also provide areas to expel fluid from cartridge 1000 to outside of cartridge 1000. Third channel 1008 may be aligned over packaged chip 802 bonded to substrate 902. In one embodiment, opening 814 over the sensor array is substantially within third channel 1008. Reference electrode 906 patterned on substrate 902 is also aligned to be within third channel 1008, according to an embodiment.

Each of first channel 1004, second channel 1006, and third channel 1008 may have channel widths between about one millimeter and three millimeters. Channel height may be around 1 millimeter. In another embodiment, one or more of first channel 1004, second channel 1006, and third channel 1008 are microfluidic channels having width and height dimensions less than 1 mm. Each of first channel 1004, second channel 1006, and third channel 1008 may have a rectangular, square, or semi-circular cross-section.

In some embodiments, one or more of first channel 1004 and second channel 1006 connect with third channel 1008. In this way, fluid flowing through first channel 1004 will flow eventually through third channel 1008, and similarly fluid flowing through second channel 1006 will flow eventually through third channel 1008. In some embodiments, third channel 1008 eventually flows into a waste chamber 1016 that collects all fluids flowing through cartridge 1000. Waste chamber 1016 may include a vent (not shown) to the atmosphere to avoid backpressure building up within the fluidic system.

In some embodiments, each inlet 1010a and 1010b includes a plug 1012a and 1012b, respectively. Plug 1012a/1012b may be a soft, compliant material that fits snuggly within inlet 1010a/1010b to seal the inlets from any fluid leakage. Plug 1012a/1012b may be a polymer material, such as polytetrafluoroethylene (PTFE), or cork. Plug 1012a/1012b may seal inlet 1010a/1010b while allowing a capillary to puncture through plug 1012a/1012b without compromising the fluidic seal. The capillary may be a needle-like tube, such as a syringe needle. The capillary may comprise a hard, rigid material such as a metal or hard plastic. The coupling of capillaries to cartridge 1000 will be described in more detail later when discussing the coupling of cartridge 1000 with an analyzer.

Cartridge 1000 includes a sample inlet 1014 arranged to introduce a sample into either first channel 1004 (as shown in FIG. 10) or second channel 1006. In one example, a blood sample may be placed into the fluidic system via sample inlet 1014. Once the sample has been introduced, sample inlet 1014 may be sealed using a cap or any other similar structure to provide a leak-proof seal around sample inlet 1014. In the illustrated channel arrangement of FIG. 10, fluid flowing through first channel 1004 from inlet 1010*a* will mix with a sample introduced via sample inlet 1014 and the mixture will flow over opening 814 and reference electrode 906 in third channel 1008. Once the sample has been delivered to the sensor array exposed via opening 814, the interaction between the biomolecules can occur and the FET Sensor sensors may be used to detect the presence of, or measure the concentration of, particular analytes in the sample. The fluid may be moved along and between the various channels using pressure driven flow. The pressure may be caused by a syringe forcing liquid or air through cartridge 1000, or by pressurized air pushing against the liquid, to name a few examples. Other examples of techniques for transporting liquid through cartridge 1000 include electro-wetting or using an on-chip peristaltic pump. In some embodiments, fluid mixing may occur within cartridge 1000 using any one of various on-chip mixing methods known in the art. The dimensions of the fluid channels of cartridge 1000 may be large enough that some fluid mixing occurs due to turbulent flow of the liquid as it moves through the channel. It should be understood that the location of sample inlet 1014 can vary. For example, sample inlet 1014 may be located directly over opening 814 such that a sample introduced into sample inlet 1014 is also introduced over the sensor array exposed via opening 814.

Once substrate 902 has been integrated into housing 1002, the sensor array accessed via opening 814 may be functionalized with various capture reagents, according to an embodiment. This process may involve flowing a liquid buffer comprising the capture reagents through third channel 1008 such that the capture reagents have the opportunity to bind to the various FET sensors in the sensor array. In another example, the capture reagents are disposed directly over opening 814 when sample inlet 1014 is positioned over opening 814. After the capture reagents have been immobilized, sample inlet 1014 may be sealed such that cartridge 1000 may be stored until it is ready to perform a biological sensing test. The capture reagents may remain within their initial buffer solution, or a fresh buffer solution may be introduced to preserve the capture reagents while cartridge 1000 awaits testing. Examples of different capture reagents and tests performed with the capture reagents are provided herein.

Figure 11:
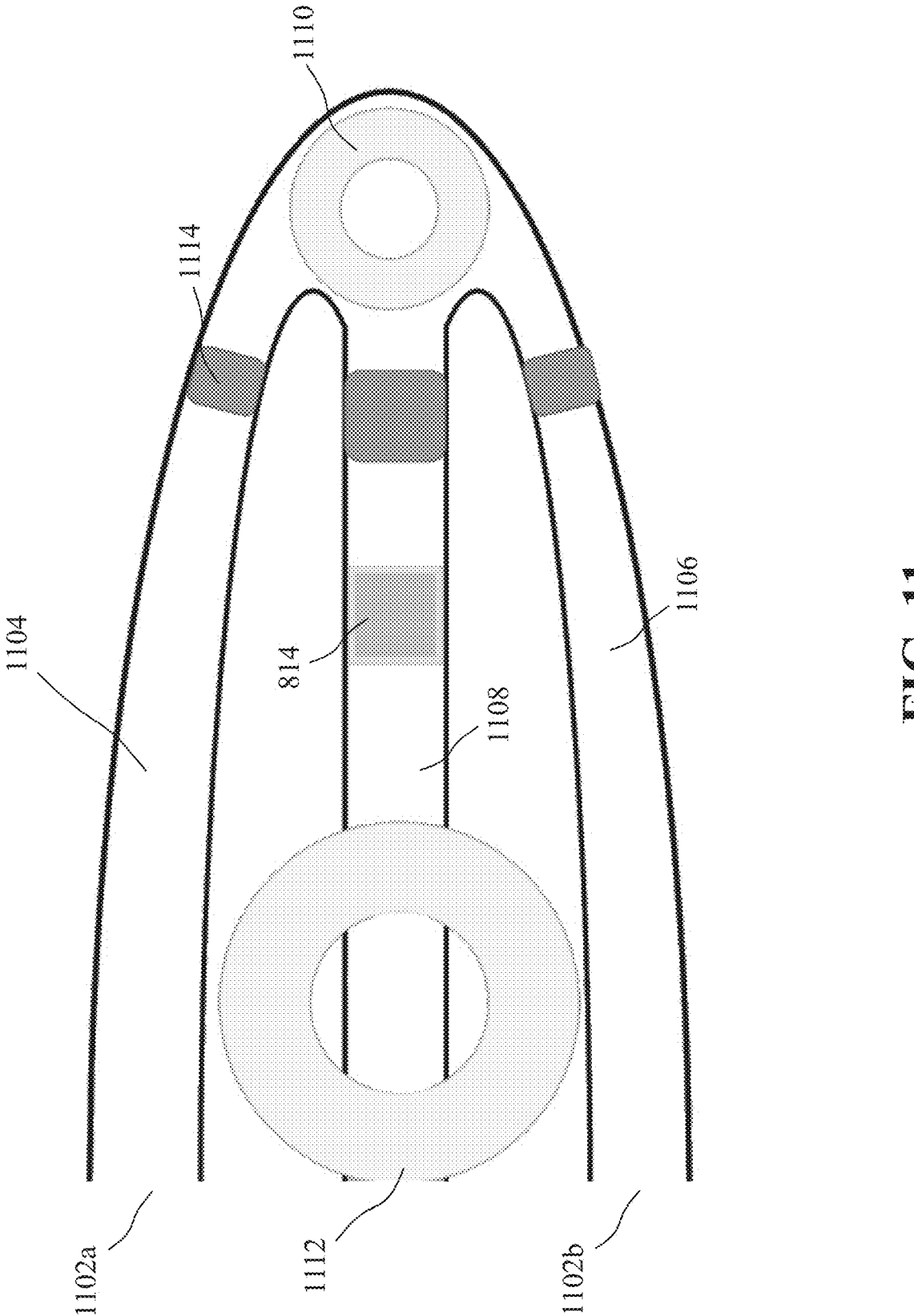
FIG. 11 is a schematic of some of the fluid channels in the exemplary fluidic cartridge.

Referring to FIG. 11, another design for the various fluidic channels of cartridge 1000 is illustrated. In this design, a first channel 1104 having a first inlet 1102*a* and a second channel 1106 having an inlet 1102*b* converge at an area having a sample inlet 1110. A third channel 1108, having opening 814 aligned within it, connects with first channel 1104 and second channel 1106 at sample inlet 1110. Opening 814 provides a pathway down to a chip to expose at least the sensor array on the chip to the fluid in third channel 1108. Fluid that flows from either first channel 1104 or second channel 1106 through third channel 1108 is ultimately collected within waste chamber 1112. Fluid may be directed towards waste chamber 1112 based on the geometry of the various channels, or by using valves to close off certain channels. Sample inlet 1110 may also be located over opening 814.

One or more of first channel 1104, second channel 1106, and third channel 1108 may include a bubble trap 1114. Bubble trap 1114 may represent an area of the fluidic channel having a suddenly greater cross-section (or a higher "ceiling") such that any air present within the solution can rise into the extra space created at bubble trap 1114. Other bubble trap designs may be utilized as well as would be understood by a person having skill in the relevant art. Removal of air bubbles from the solution before it reaches the sensor array beneath opening 814 may be important to ensure accurate sensing results.

Figure 12:
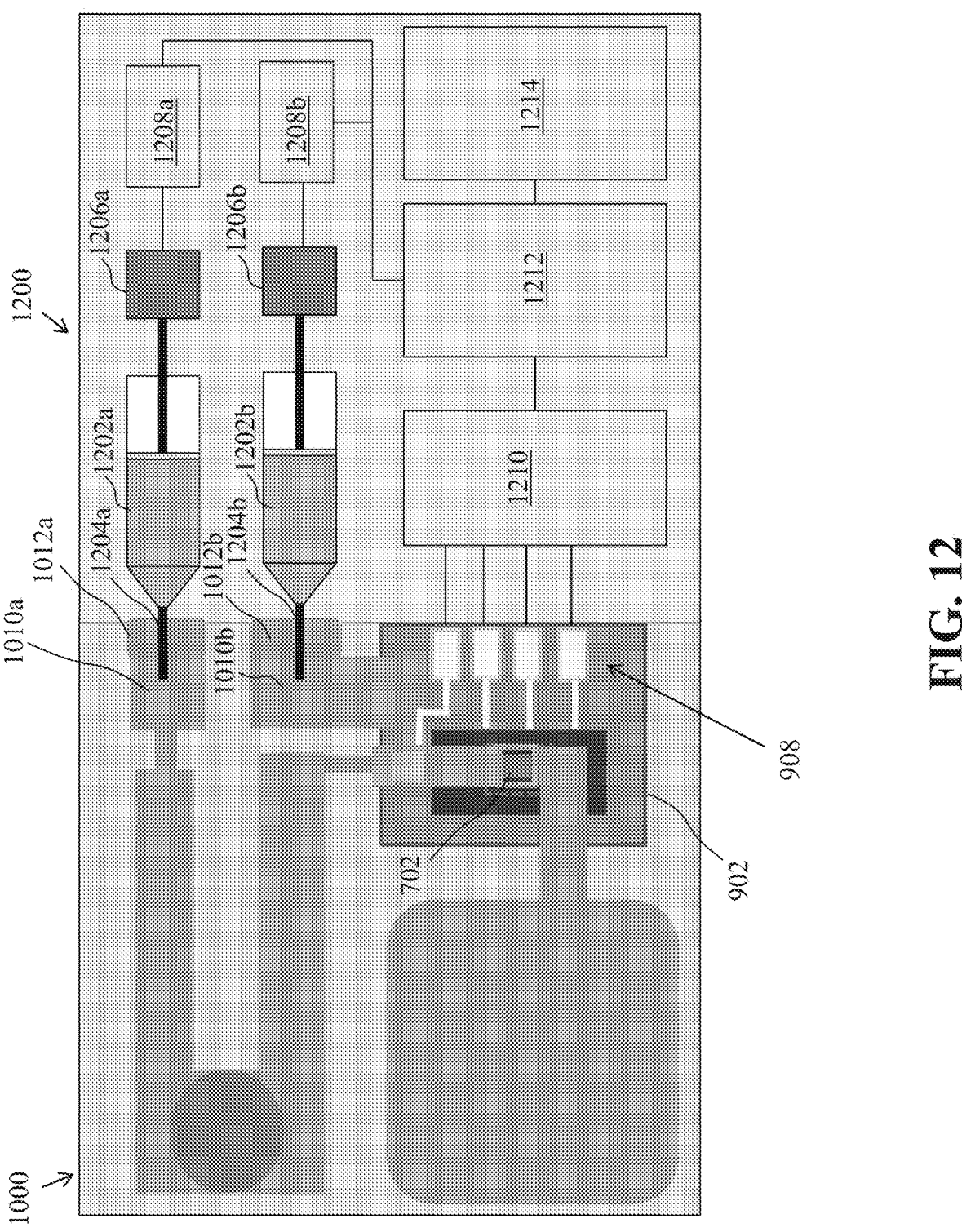
FIG. 12 is a schematic of the exemplary fluidic cartridge coupled to an analyzer.

Referring to FIG. 12, cartridge 1000 is illustrated being coupled to an analyzer 1200 for performing the biological sensing. Cartridge 1000 may be brought into physical contact with analyzer 1200 by, for example, pressing cartridge 1000 against a receiving port of analyzer 1200. The receiving port of analyzer 1200 may include electrical pads to form ohmic contacts to some or all of edge connectors 908. An edge of substrate 902 may fit snuggly into a receiving port of analyzer 1200 such that edge connectors 908 press against corresponding conductive pads of analyzer 1200. Other methods of assembling cartridge 1000 and analyzer 1200 include snapping them together, plugging one into the other, among others. Analyzer 1200 may be small enough to be easily portable and may fit into the palm of an adult human hand.

In some embodiments, analyzer 1200 includes at least a first syringe 1202*a* and a second syringe 1202*b*. Each of first syringe 1202*a* and second syringe 1202*b* may include buffers or other fluids used during the operation of cartridge 1000. Syringes 1202*a*/1202*b* each include a needle 1204*a*/1204*b* that may be aligned to extend into space away from a remaining portion of analyzer 1200. In some embodiments, needle 1204*a*/1204*b* may be aligned such that pressing cartridge 1000 against a receiving port of analyzer 1200 causes needle 1204*a*/1204*b* to puncture through corresponding plug 1012*a*/1012*b* and into inlet 1010*a*/1010*b*. In this embodiment, needle 1204*a*/1204*b* is one example of a capillary that punctures through corresponding plug 1012*a*/1012*b*. Thus, a leak-proof seal is created to transfer solution from each syringe 1202*a*/1202*b* into the corresponding inlet 1010*a*/1010*b* of cartridge 1000. It should be understood that although this description describes only two syringes aligned with two input ports, any number of syringes and fluidic input ports may be used, including an example where only one syringe is used to couple with a single inlet. Each syringe 1202*a*/1202*b* may be preloaded with solution for use in various tests. In another embodiment, each syringe 1202*a*/1202*b* may be easily removed and replaced with a different syringe by a user.

Each syringe 1202*a*/1202*b* may have its associated plunger controlled via a corresponding actuator 1206*a*/1206*b*. Examples of actuator 1206*a*/1206*b* include a stepper motor or an induction motor. The speed at which actuators 1206*a*/1206*b* depress the plungers of syringes 1202*a*/1202*b* will directly affect the flow rate of the solution within the fluidic channels of cartridge 1000. Actuator 1206*a*/1206*b* may be controlled via motor control module 1208*a*/1208*b*. Motor control module 1208*a*/1208*b* includes the circuitry required to generate voltages for controlling the speed and operation of actuator 1206*a*/1206*b*, as would be understood by a person skilled in the relevant art.

All electrical connections made to edge connectors 908 of cartridge 1000 may be routed to sensing electronics 1210. Sensing electronics 1210 may include any number of discrete circuits, integrated circuits, and discrete analog circuit components that are designed to both provide and receive numerous different electrical signals between sensing electronics 1210 and edge connectors 908. For example, sensing electronics 1210 may be configured to provide power, ground, and clock signals to edge connectors 908, which may be subsequently used to power and operate the sensor array and other electronics on chip 702. Sensing electronics 1210 may also provide various voltage bias levels for activating the gates of particular FET Sensors within the sensor array. Sensing electronics 1210 may receive signals that represent drain currents measured from particular FET Sensors, and signals that represent outputs from temperature sensors on chip 702. Sensing electronics 1210 may store this received data in a memory, or may use the received data to alter the voltage bias levels, or to change an amount of heat generated by heaters on chip 702. Generally, sensing electronics 1210 control all signaling related to the biosensing performed by the sensor array of cartridge 1000.

In some embodiments, analyzer 1200 also includes a processor 1212 that controls the functions and timing of each of the other modules of analyzer 1200, such as motor control module 1208a/1208b and sensing electronics 1210. Processor 1212 may be any type of central processing unit (CPU) or microcontroller and may be programmable by a user to perform certain functions related to the operation of analyzer 1200. Processor 1212 may be configured to analyze signals received from sensing electronics 1210 to determine a concentration level of a given analyte from the sample in cartridge 1000. Data related to the determined concentration levels may be stored in a memory of analyzer 1200. In another embodiment, sensing electronics 1210 determines a concentration level of a given analyte from the sample in cartridge 1000, and is further configured to store data related to the determined concentration levels in a memory of analyzer 1200.

In some embodiments, analyzer 1200 includes a communication module 1214 that is designed to communicate data to an external processing device. Processor 1212 may be electrically coupled with communication module 1214 to control data transfer. The communication may be wired or wireless. Examples of wired communication include data transfer via a network cable or a universal serial bus (USB) cable. Wireless communication may include radio RF transmission, Bluetooth, WiFi, 3G, or 4G. Communication module 1214 may also be designed to receive data from the external processing device. For example, a program for how to operate the various components of analyzer 1200 may be transmitted to communication module 1214 and executed by processor 1212. Communication module 1214 may include any number of well-known hardware elements to facilitate analog and/or digital data transmission and reception.

After a biosensing test has been performed, cartridge 1000 may be removed from analyzer 1200 and discarded. Additionally, syringes 1202a/1202b may be removed from analyzer 1200 and discarded. Thus, all reagents remain contained within either cartridge 1000 or syringes 1202a/1202b and no contamination of any other part of analyzer 1200 occurs. In this way, a single analyzer 1200 may be reused to test any number of additional cartridges, where each cartridge may be individually functionalized with different capture reagents to perform a different biosensing test.

In another embodiment, syringes 1202a/1202b are integrated on cartridge 1000, and the coupling between cartridge 1000 and analyzer 1200 aligns the associated plungers of syringes 1202a/1202b with actuators 1206a/1206b on analyzer 1200. In this embodiment, analyzer 1200 is completely free of any reagent-carrying containers.

In another embodiment, cartridge 1000 includes one or more capillaries that are punctured through corresponding plug 1012a/1012b. In this embodiment, when coupling occurs between cartridge 1000 and analyzer 1200, the capillaries fluidically couple with the remainder of syringes

1202a/1202b in analyzer 1200. After a biosensing test has been performed, cartridge 1000 along with its capillaries may be removed from analyzer 1200 and discarded.

Figure 13:
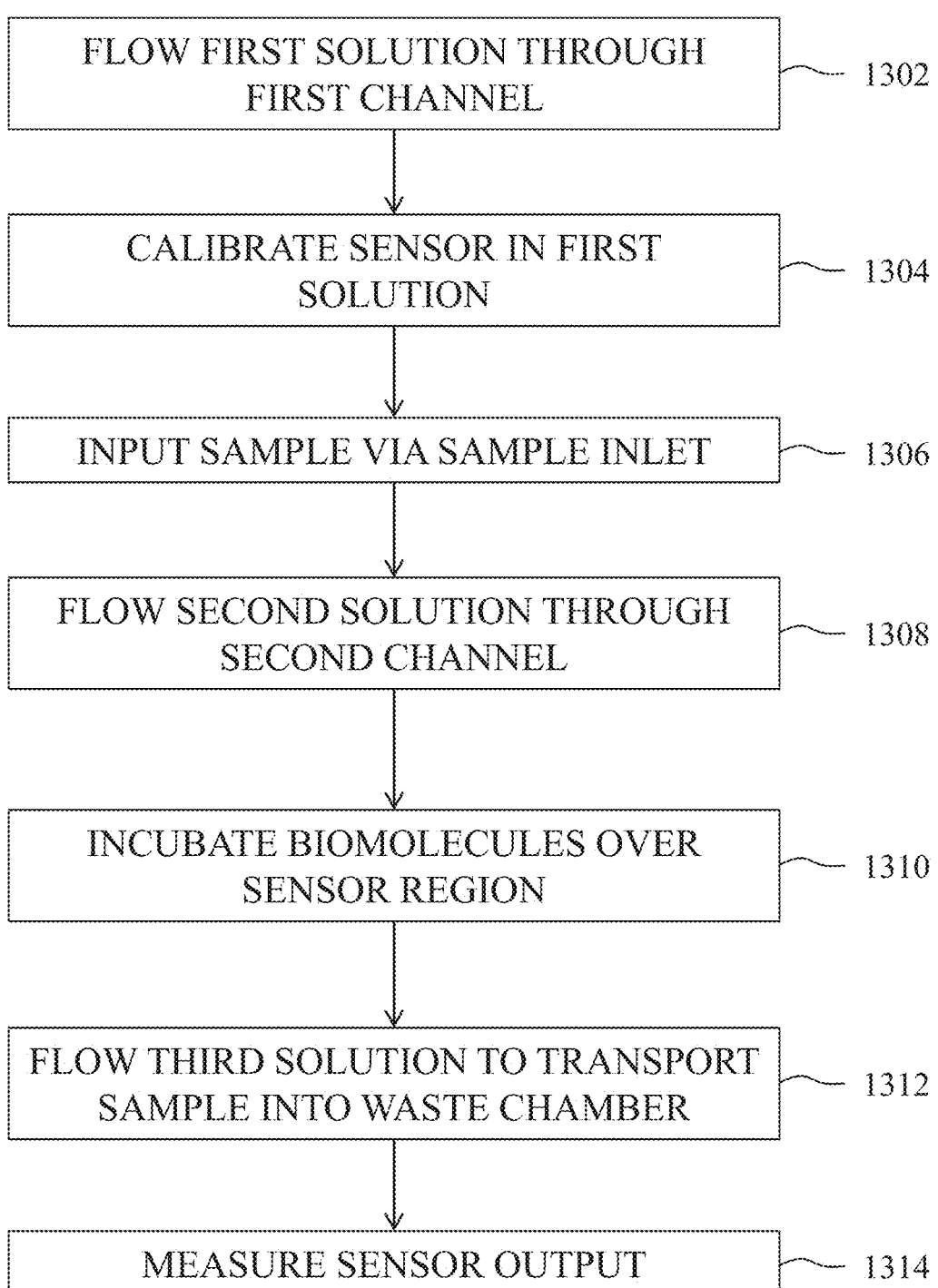
FIG. 13 is a flow diagram of an exemplary method of using the fluidic cartridge.

Referring to FIG. 13, an example method 1300 is presented. Method 1300 may be performed by analyzer 1200 after cartridge 1000 has been coupled to analyzer 1200. Other operations relating to fluid handling and electrical measurement not illustrated in method 1300 may be performed either before, between, or after the illustrated operations of method 1300. The various operations of method 1300 may be performed in a different order than the one illustrated. In an embodiment, method 1300 is performed after capture reagents have already been immobilized within cartridge 1000.

At block 1302, a first solution flows through a first channel of a cartridge. The first solution may enter the cartridge via an inlet coupled to the first channel. The first solution may be provided by a syringe having its needle puncturing through a plug disposed at the inlet of the first channel. The first solution may include a buffer solution to provide a stable pH environment.

At block 1304, the dual gate back-side sensing FET Sensors of the sensor array are calibrated in the first solution. The calibration may be performed to measure a noise or background signal of the various FET Sensors. This measurement may be stored and later subtracted from the measured signal when detecting biomolecules to try and reduce the noise and achieve a clearer detection signal. The first solution must be present over the sensor array and the reference electrode patterned within the main detection channel to perform the calibration. In some embodiments, the first solution is not flowing during the calibration measurement. In some embodiments, the calibration measurement represents the baseline threshold voltage for the FET sensors.

At block 1306, a sample is input into the fluidic network of the cartridge via a sample inlet. The sample may be any liquid sample, including a blood sample. In some embodiments, the sample is a semi-solid sample that dissociates within solution. After the sample has been input via the sample inlet, the sample inlet may be sealed by using a cap or other similar structure.

At block 1308, a second solution flows through a second channel of the cartridge. The second solution may be the same solution as the first solution. The second solution may cross paths with the sample input into the fluidic system at block 1306, and mix with the sample. The mixture of the sample and the second solution may then flow through the second channel and into the main detection channel where the sensor array is located. The second solution may be a buffer solution. In one example, the second solution is a lysing buffer solution. The second solution may be moved along and between the various channels using pressure driven flow. The pressure may be caused by a syringe forcing liquid or air through the cartridge, or by pressurized air pushing against the second solution, to name a few examples. Other examples of techniques for transporting the second solution through the cartridge include electro-wetting or using an on-chip peristaltic pump.

At block 1310, the biomolecules present within the sample are incubated over the sensor array. Incubation may last for any given amount of time, for example, between 30 seconds and 10 minutes. During incubation, the sample mixed with the second solution may not be flowing, or may be flowing at a very slow flow rate. The flow rate may be designed such that fresh solution is presented over the sensor array over time, but the flow is not too strong to cause damage to the capture reagents or to not allow for the binding reactions to occur.

At block 1312, after the incubation time has expired, a third solution flows through the first channel of the cartridge and through the main detection channel to push substantially all of the sample mixed with the second solution into the waste chamber. The third solution may be injected through the main detection channel for a given period of time to ensure that the sample has been cleared from the main detection channel. The third solution used in block 1312 should ideally be the same solution as the first solution. In another embodiment, the third solution is different from the first solution. The third solution may be a buffer solution.

At block 1314, the output from the sensor array is measured to determine if any binding reactions occurred. The sensor output may be a drain current measured from one or more of the dual gate back-side sensing FET Sensors in the sensor array. The measured drain current may be compared to a drain current measured during calibration of the same sensor in block 1304. If the threshold voltage (e.g., roughly corresponding to the voltage needed to turn on the FET and cause the drain current to flow) has changed from when the sensor was calibrated, then it may be determined that a binding reaction has occurred and that a target analyte was present in the sample. The amount, and sign, of the change in threshold voltage may depend on numerous factors, such as whether the dual gate back-side sensing FET Sensor was an n-channel device or a p-channel device, the type of analyte being detected and the amount of positive or negative charge associated with the analyte. In another example, the measured output from the sensor array is the threshold voltage itself, which may be compared to a threshold voltage measured during calibration of the same sensor in block 1304.

Chemistry, Biology and Interface

The apparatus, systems, and methods of the invention as described in this application can be used to detect and/or monitor interactions between various entities. These interactions include biological and chemical reactions to detect target analytes in a test sample. As an example, reactions, including physical, chemical, biochemical, or biological transformations, can be monitored to detect generation of intermediates, byproducts, products, and combinations thereof. In addition the apparatus, systems, and methods of the invention can be used to detect these reactions in various assays as described herein, including, but not limited to, circulating tumor cell assays used in liquid biopsies and chelation assays to detect the presence of heavy metals and other environmental pollutants. Such assays and reactions can be monitored in a single format or in an array format to detect, e.g., multiple target analytes.

Biological Sensing Examples with DGBSS FET Sensor

Figure 14:
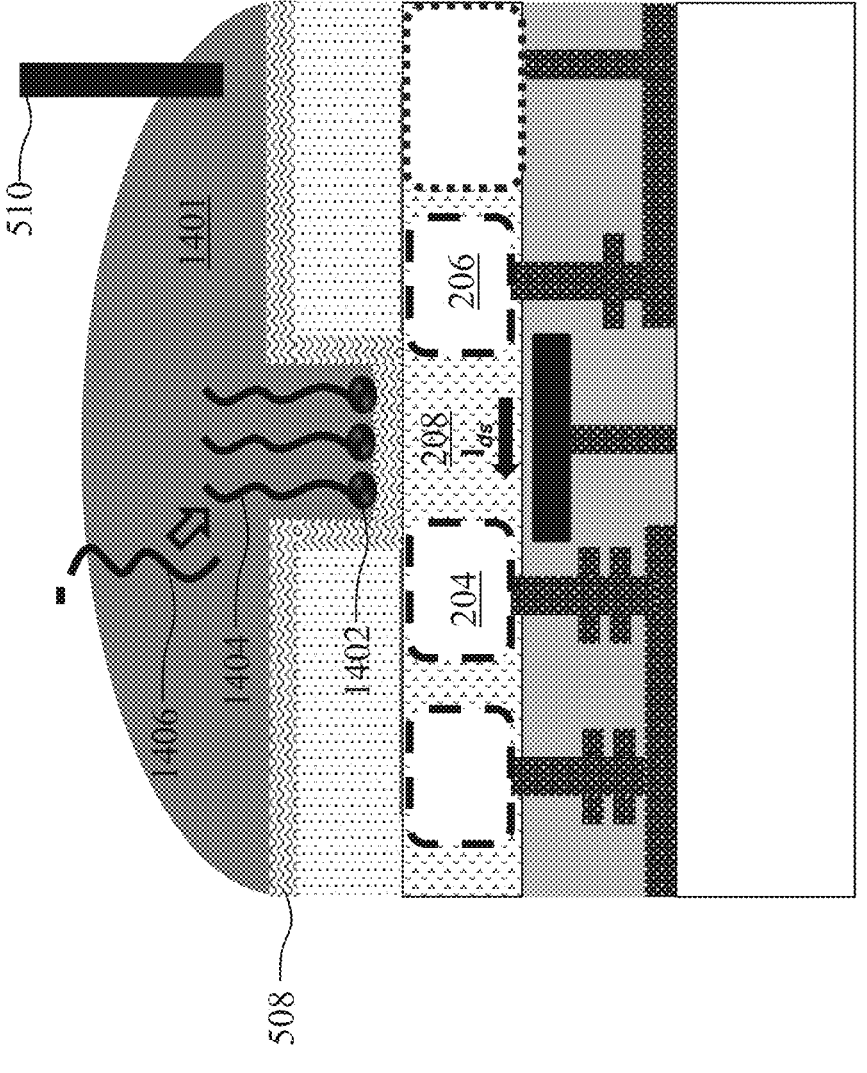
FIG. 14 is a cross-sectional view of an exemplary dual gate back-side sensing bioFET detecting DNA.

Referring to FIG. 14, an example biosensing test is performed using the dual gate back-side sensing FET Sensor described above. Probe DNA 1404 (an example of a capture reagent) is bound to interface layer 508 via a linking molecule 1402. Linking molecule 1402 may have a reactive chemical group that binds to a portion of interface layer 508. An example of linking molecules include thiols. Linking molecules may also be formed via silanization of the surface of interface layer 508, or by exposing the surface of interface layer 508 to ammonia ($NH_3$) plasma, in order to form reactive $NH_2$ groups on the surface. The silanization process involves sequentially exposing the surface of interface layer 508 to different chemicals to build up covalently-bound molecules on the surface of interface layer 508, as would be generally understood to a person skilled in the relevant art. Probe DNA 1404 represent single stranded DNA. According to an embodiment, linking molecule 1402 is bound to interface layer 508 before any steps of method 1300 are performed. Probe DNA 1404 may also be bound to linking molecule 1402 before any steps of method 1300 are performed. In another example, probe DNA 1404 is bound to linking molecule 1402 at block 1302 of method 1300.

The dual gate back-side sensing FET sensor illustrated in FIG. 14 is one FET within a sensor array that would exist on a chip, such as chip 702 described above, according to an embodiment. Linking molecule 1402 may be bound to interface layer 508 before a wafer containing chip 702 is diced to separate chip 702 from the wafer.

Probe DNA 1404 may be immobilized on interface layer 508 prior to subjecting the FET Sensor to sample 1401. Sample 1401 may include the matching single stranded DNA sequence 1406 that binds strongly to its matching probe DNA 1404. The binding of additional DNA increases the negative charge present on interface layer 508, and directly above channel region 208 of the FET Sensor.

Figure 15B:
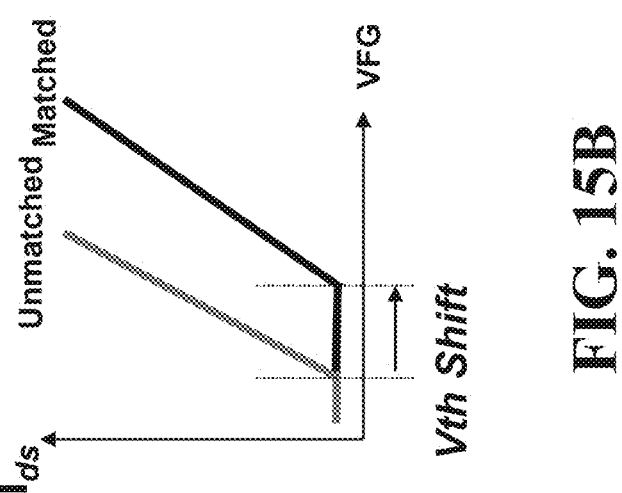
FIG. 15B illustrates a change in threshold voltage for the exemplary dual gate back-side sensing bioFET based on matched analyte binding.
Figure 15A:
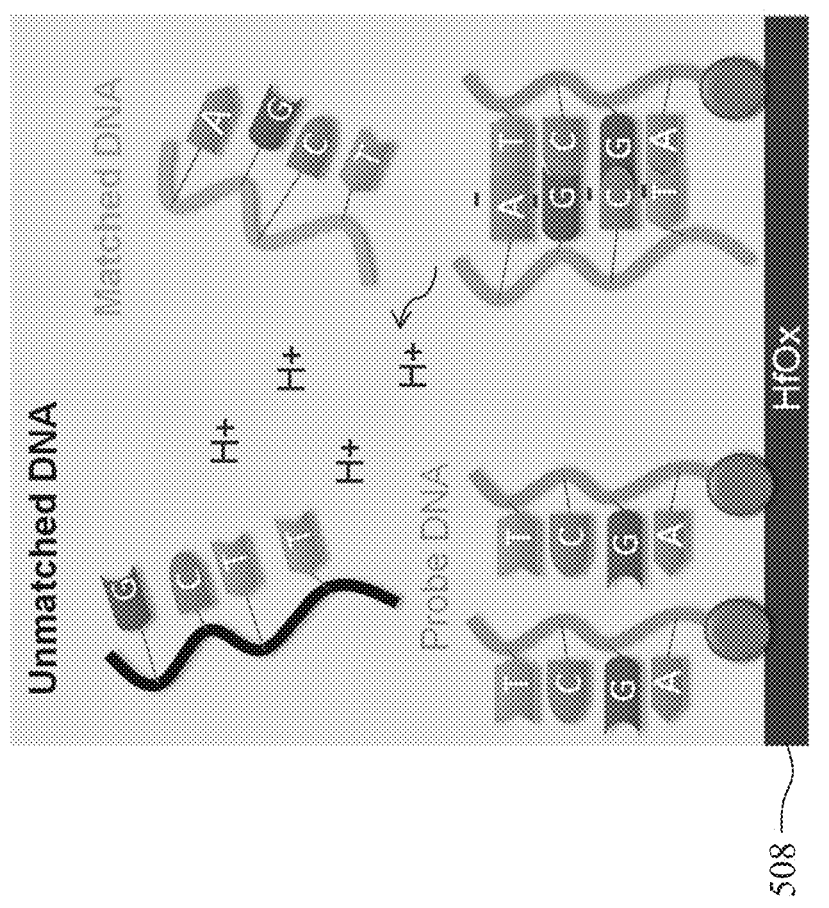
FIG. 15A illustrates the binding mechanics of DNA on a receptor surface.

The DNA binding is illustrated conceptually in FIG. 15A. Here probe DNA having nucleic acid sequence TCGA binds to its complementary matched strand having nucleic acid sequence AGCT. Any unmatched sequences will not hybridize with the probe DNA sequences. The binding of the matching DNA increases the negative charge built up at the interface of interface layer 508. In the example illustrated in FIG. 15A, interface layer 508 is hafnium oxide.

FIG. 15B illustrates a shift in the threshold voltage of the dual gate back-side sensing FET Sensor when matching DNA is bound to the surface of interface layer 508. Briefly, voltage is applied to fluid gate 510 until the FET Sensor "turns on" and current flows between drain region 206 and source region 204. When more negative charge is present at interface layer 508 due to complementary DNA binding, a higher voltage is required to form the conductive inversion layer within the channel region 208. Thus, according to an embodiment, a higher voltage may be applied to fluid gate 510 before the FET Sensor conducts and Ids current flows. This difference in threshold voltage may be measured and used to determine not only the presence of the target matching DNA sequence, but also its concentration. It should be understood that a net positive accumulated charge at interface layer 508 would cause the threshold voltage to decrease rather than increase. Additionally, the change in threshold voltage will have the opposite sign for an n-channel FET as compared to a p-channel FET.

Figure 16:
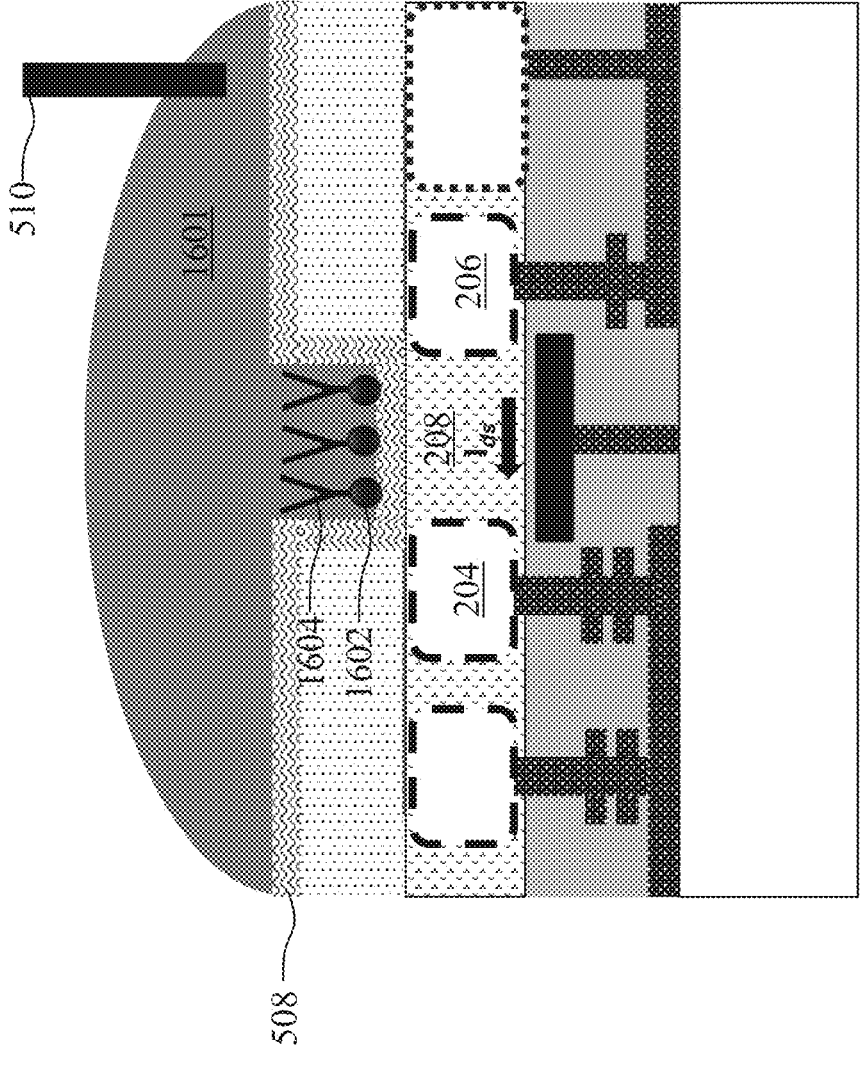
FIG. 16 is a cross-sectional view of an exemplary dual gate back-side sensing bioFET having antibodies immobilized on its sensing layer.

Referring to FIG. 16, another example biosensing test is performed using the dual gate back-side sensing FET Sensor. Probe antibodies 1604 (another example of capture reagents) are bound to interface layer 508 via linking molecules 1602. Linking molecules 1602 may have a reactive chemical group that binds to a portion of interface layer 508. A sample solution 1601 may be provided over probe antibodies 1604 to determine if the matching antigens are present within sample solution 1601. According to an embodiment, linking molecules 1602 are bound to interface layer 508 before any steps of method 1300 are performed. Probe antibodies 1604 may also be bound to linking molecules 1602 before any steps of method 1300 are performed. In another example, probe antibodies 1604 are bound to linking molecules 1602 at block 1302 of method 1300.

Figure 17:
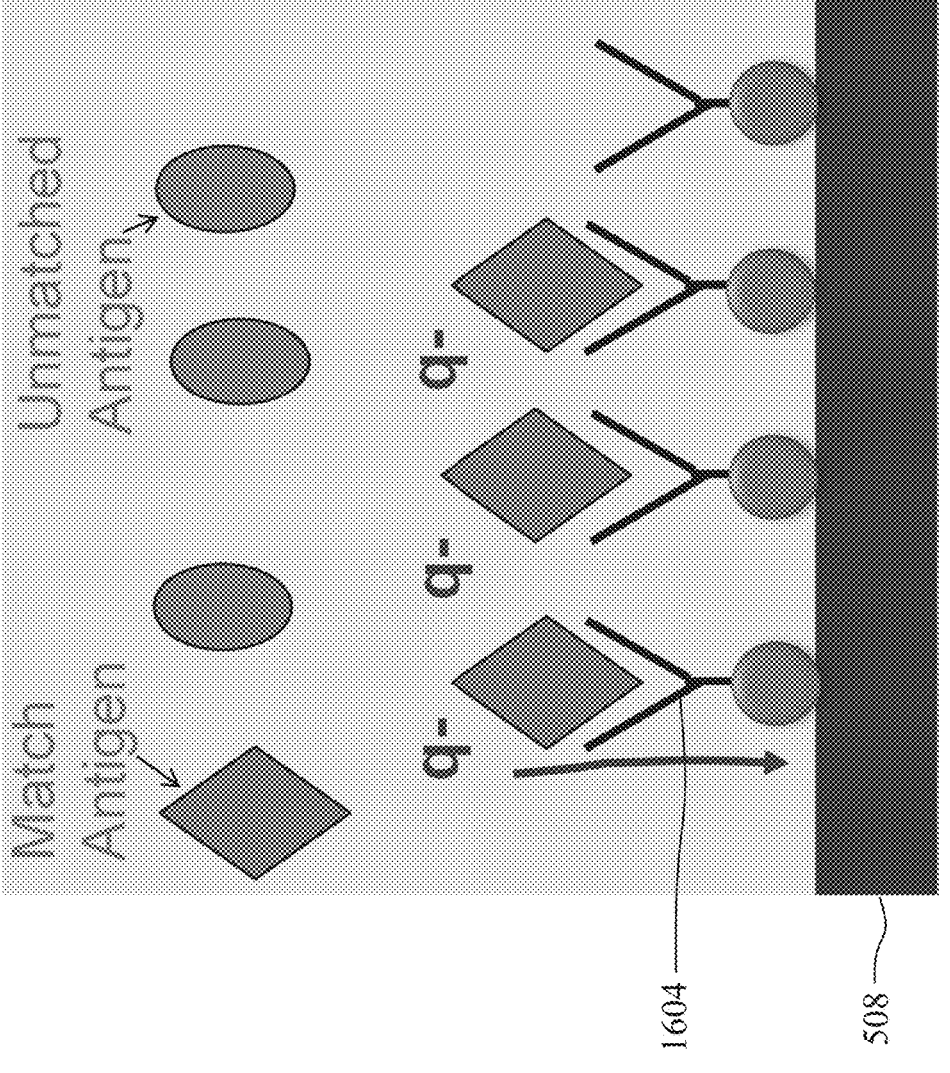
FIG. 17 illustrates the binding mechanics of antigens and antibodies on a receptor surface.

Referring to FIG. 17, the binding process of matching antigens to probe antibodies 1604 is illustrated. Here, matching antigens will bind to the immobilized probe antibodies while unmatched antigens will not bind. Similar to the DNA hybridization process described above, the matching antigens will change the accumulated charge present at interface layer 508. The shift in threshold voltage due to the accumulated charge from matching antibodies binding to the probe antibodies is measured in substantially the same way as already discussed above with reference to FIG. 15B.

Final Remarks

It is to be appreciated that the Detailed Description section, and not the Abstract of the Disclosure section, is intended to be used to interpret the claims. The Abstract of the Disclosure section may set forth one or more but not all exemplary embodiments of the present invention as contemplated by the inventor(s), and thus, is not intended to limit the present invention and the subjoined claims in any way.

It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the subjoined claims and their equivalents.

What is claimed is:

1. A system, comprising:
a fluidic cartridge, comprising:
a substrate;
a biological field effect transistor (BioFET) sensor array disposed on the substrate,
first, second, and third fluidic channels disposed on the same surface plane and coupled to the BioFET sensor array, and
a reference electrode disposed on the substrate and on the same surface plane as the BioFET sensor array:
an analyzer, comprising:
first and second syringes coupled to first and second fluidic channels;
a first needle aligned with the first syringe and a first fluid inlet of the first fluidic channel;
a second needle aligned with the second syringe and a second fluid inlet of the second fluidic channel;
first and second actuators configured to control the first and second syringes, respectively;
a sensing module coupled to the BioFET sensor array, wherein the sensing module is configured to activate the BioFET sensor array; and
a processor electrically coupled to the sensing module and the first and second actuators, wherein the processor is configured to determine a concentration level of a given analyte from a sample in the fluidic cartridge based on signals received from the BioFET sensor array.

2. The system of claim 1, wherein the first and second syringes are configured to deliver buffer solutions to the BioFET sensor array through the first and second fluidic channels.

3. The system of claim 1, wherein the first needle is configured to deliver a buffer solution to the first fluidic channel through a first plug disposed within the first fluid inlet.

4. The system of claim 1, wherein the third fluidic channel comprises an opening on the BioFET sensor array and adjacent to the reference electrode.

5. The system of claim 1, wherein the fluidic cartridge further comprises a conductive pad disposed on the substrate, and wherein the reference electrode is connected to the sensing module through the conductive pad.

6. A system, comprising:
a fluidic cartridge, comprising:
a biological field effect transistor (BioFET) sensor array,
first, second, and third fluidic channels disposed on a same surface plane and coupled to the BioFET sensor array, and
a reference electrode disposed in the third fluidic channel and on the same surface plane as the BioFET sensor array;
an analyzer, comprising:
a first needle of a first syringe aligned parallel to the surface plane and positioned inside an inlet of the first fluidic channel;
a second needle of a second syringe aligned parallel to the surface plane and positioned inside an inlet of the second fluidic channel;
first and second actuators configured to control the first and second syringes, respectively;
a sensor configured to send and receive signals from the BioFET sensor array; and
a processor configured to determine a concentration level of a given analyte from a sample in the fluidic cartridge based on the signals received from the BioFET sensor array.

7. The system of claim 6, wherein the first syringe is detachable from the analyzer.

8. The system of claim 6, wherein the first syringe is configured to hold and deliver a buffer solution to the first fluidic channel.

9. The system of claim 6, wherein the first needle is configured to deliver a buffer solution to the first fluidic channel through a plug disposed in the first fluidic channel.

10. The system of claim 6, wherein the first and second syringes and the first and second fluidic channels extend in directions parallel to a substrate of the BioFET sensor array.

11. The system of claim 6, wherein the sensor is configured to activate the BioFET sensor array.

12. The system of claim 6, further comprising a controller configured to control the first and second actuators.

13. The system of claim 12, wherein the processor is coupled to the controller.

14. The system of claim 6, further comprising a memory configured to store data related to the concentration level of a given analyze determined by the processor.

15. The system of claim 6, further comprising a communications module configured to transmit data wirelessly to an external processing device.

16. The system of claim 6, wherein the analyzer and the fluidic cartridge are portable.

17. A system, comprising:
a biological field effect transistor (BioFET) sensor array;
first, second, and third fluidic channels disposed on the same surface plane and coupled to the BioFET sensor array;
a reference electrode disposed between the first and third fluidic channels and on a same surface plane as the BioFET sensor array;
a waste chamber coupled to the first fluidic channel through the third fluidic channel;
a first syringe configured to introduce a first solution into the BioFET sensor array through the first fluidic channel;

a second syringe configured to introduce a second solution to the BioFET sensor array through the second fluidic channel;

a sensor configured to measure a first signal associated with the first solution and a second signal associated with the second solution; and a processor configured to determine a presence of an analyte in a sample in the BioFET sensor array based on the first and second signals.

18. The system of claim 17, further comprising a sample inlet configured to introduce the sample into the BioFET sensor array.

19. The system of claim 17, wherein the BioFET sensor array comprises an array of dual gate back-side sensing FETs.

20. The system of claim 17, further comprising first and second actuators configured to control the first and second syringes, respectively.

* * * * *